US012708476B2

(12) United States Patent
Nguyen et al.

(10) Patent No.: US 12,708,476 B2
(45) Date of Patent: Aug. 18, 2026

(54) LIGAMENT RETRACTOR

(71) Applicant: Optimotion Implants LLC, Orlando, FL (US)

(72) Inventors: Vuong Binh Nguyen, Windermere, FL (US); Dinesh V. Koka, Winter Springs, FL (US)

(73) Assignee: Optimotion Implants LLC, Orlando, FL (US)

( * ) Notice: Subject to any disclaimer, the term of this patent is extended or adjusted under 35 U.S.C. 154(b) by 0 days.

(21) Appl. No.: 18/950,106

(22) Filed: Nov. 17, 2024

(65) Prior Publication Data

US 2025/0072991 A1 Mar. 6, 2025

Related U.S. Application Data

(63) Continuation of application No. 17/211,530, filed on Mar. 24, 2021, now Pat. No. 12,290,411, which is a continuation-in-part of application No. 16/803,501, filed on Feb. 27, 2020, now Pat. No. 11,642,117.

(60) Provisional application No. 62/812,245, filed on Feb. 28, 2019.

(51) Int. Cl.

| | |
|---|---|
| ***A61B 90/00*** | (2016.01) |
| ***A61B 17/02*** | (2006.01) |
| *A61B 17/00* | (2006.01) |

(52) U.S. Cl.

CPC ............ *A61B 90/08* (2016.02); *A61B 17/025* (2013.01); *A61B 2017/0046* (2013.01); *A61B 2017/0268* (2013.01); *A61B 2090/08021* (2016.02)

(58) Field of Classification Search

CPC .................. A61B 90/08; A61B 17/025; A61B 2017/0046; A61B 2017/0268; A61B 2090/08021

See application file for complete search history.

(56) References Cited

U.S. PATENT DOCUMENTS 5,334,194 A * 8/1994 Mikhail ............... A61B 17/025 606/88

FOREIGN PATENT DOCUMENTS

EP 1559375 A1 * 8/2005 ........... A61B 17/154

* cited by examiner

*Primary Examiner* — Nicholas J Plionis

(74) *Attorney, Agent, or Firm* — David Meibos; Maywood IP Law

(57) ABSTRACT

A retractor assembly may include a retractor removably coupled with a retractor handle. The retractor may include a handle connection feature, a retractor shaft, an arcuate projection having a convex retractor surface and a cutting shield surface, and a guide projection having an aperture shaped to receive at least a portion of a femoral condyle therein to position the retractor relative to a tibial plateau. The retractor handle may include a handle portion and a retractor connection feature. The retractor may be placed on a lateral side of a medial collateral ligament of a knee joint to retract the medial collateral ligament away from a tibial plateau of the knee joint and protect the medial collateral ligament during a tibial plateau resection procedure.

7 Claims, 23 Drawing Sheets

100
133
160
162
137
150
136

137
100
150
160
134
136

100
135
138
139
134

200
220
235
234
236
233
231
230

200
230
232
234
233
220
236
235

LIGAMENT RETRACTOR

CROSS-REFERENCE TO RELATED APPLICATIONS

This application is a continuation of U.S. patent application Ser. No. 17/211,530 filed on Mar. 24, 2021, entitled LIGAMENT RETRACTOR, which is a continuation-in-part of U.S. patent application Ser. No. 16/803,501 filed on Feb. 27, 2020, entitled LIGAMENT RETRACTOR, which issued on May 9, 2023 as U.S. Pat. No. 11,642,117, which claims the benefit of U.S. Provisional Patent Application No. 62/812,245 filed on Feb. 28, 2019, entitled LIGAMENT RETRACTOR. The above-referenced documents are hereby incorporated by reference in their entirety.

TECHNICAL FIELD

The present disclosure relates to surgical instruments, systems, and methods. More specifically, the present disclosure relates to improved surgical instruments, systems, and methods for retracting ligaments in order to facilitate surgical procedures, such as a knee joint arthroplasty.

BACKGROUND

Joint arthroplasty procedures are surgical procedures in which one or more articulating surfaces of a joint are replaced with prosthetic articulating surfaces. Such procedures are becoming increasingly commonplace, particularly for knee joints. An arthroplasty procedure for a knee joint can include implanting a tibial prosthesis to replace the articulating surfaces of the tibia. This may or may not be performed along with replacement of the articulating surfaces of the femur and/or the patella.

For a successful knee joint arthroplasty, it is important to protect certain ligaments of the knee joint from accidental damage during bone resection operations performed during a knee joint arthroplasty procedure. For example, performing a tibial plateau resection operation can carry an increased risk of accidentally damaging or cutting the medial collateral ligament, especially when a surgeon blindly approaches the medial collateral ligament from the lateral side with a saw blade during a tibial plateau resection procedure.

Accordingly, surgical instruments, systems, and methods that can reduce or eliminate the risk of accidentally damaging or cutting ligaments during a surgical procedure would be desirable.

SUMMARY

The various surgical instruments, systems, and methods of the present disclosure have been developed in response to the present state of the art, and in particular, in response to the problems and needs in the art that have not yet been fully solved by currently available surgical instruments, systems, and methods. The surgical instruments, systems, and methods of the present disclosure may provide a reduced risk of accidentally damaging or cutting ligaments during a bone resection operation.

According to some embodiments, a retractor assembly may include a retractor and a retractor handle. The retractor may include a retractor shaft, a handle connection feature, and a retractor member. The retractor member may be disposed at the distal end of the retractor shaft and may include an arcuate projection having a proximal end coupled to the distal end of the retractor shaft, a distal end transversely projecting away from a first longitudinal axis, a superior surface, an inferior surface, a retractor surface extending intermediate the superior surface and the inferior surface and including a convex curvature, and a cutting shield surface located opposite the retractor surface extending intermediate the superior surface and the inferior surface. The retractor handle may be configured to removably couple with the retractor and may include a handle portion, a handle shaft coupled to the handle portion, and a retractor connection feature coupled to the handle shaft. The retractor connection feature may be configured to removably couple with the handle connection feature to removably couple the retractor handle with the retractor.

In some embodiments of the retractor assembly, the retractor member may also include a guide projection coupled to the cutting shield surface and projecting toward the first longitudinal axis. The guide projection may include a superior surface, an inferior surface, and an aperture formed through the guide projection between the superior surface and the inferior surface. The aperture may be shaped to receive at least a portion of a femoral condyle therein to position the retractor member relative to a tibial plateau.

In some embodiments of the retractor assembly, the retractor shaft may also include a first shaft portion extending along the first longitudinal axis, a second shaft portion extending along a second longitudinal axis, and a third shaft portion extending along a third longitudinal axis. The second shaft portion may be intermediate the first shaft portion and the second shaft portion, and the third shaft portion may be offset from the first shaft portion.

In some embodiments of the retractor assembly, the handle connection feature may be coupled to the third shaft portion.

In some embodiments of the retractor assembly, the retractor connection feature may include a locking feature configured to secure the retractor handle to the retractor by engaging the handle connection feature.

In some embodiments of the retractor assembly, the handle connection feature may include a hex key and a retention slot formed in the hex key.

In some embodiments of the retractor assembly, the locking feature may include a locking sleeve, a hex socket disposed within the locking sleeve, and one or more ball detents at least partially disposed within an interior space of the hex socket. The hex socket may be configured to receive the hex key, and the one or more ball detents may be configured to engage the retention slot that is formed in the hex key to secure the retractor handle to the retractor.

According to some embodiments, a retractor may include a retractor shaft, a retractor member, and a guide projection. The retractor member may be disposed at the distal end of the retractor shaft and may include an arcuate projection having a proximal end coupled to the distal end of the retractor shaft, a distal end transversely projecting away from a first longitudinal axis, a superior surface, an inferior surface, a retractor surface extending intermediate the superior and inferior surfaces and having a convex curvature, and a cutting shield surface located opposite the retractor surface and extending intermediate the superior and inferior surfaces. The guide projection may be coupled to the cutting shield surface and may project toward the first longitudinal axis. The guide projection may include a superior surface, an inferior surface, and an aperture formed through the guide projection between the superior surface and the inferior surface. The aperture may be shaped to receive at least a portion of a femoral condyle therein to position the retractor member relative to a tibial plateau.

In some embodiments of the retractor, the superior surface and the inferior surface of the guide projection may be configured to taper toward each other moving from the proximal end of the arcuate projection toward the distal end of the arcuate projection.

In some embodiments of the retractor, the guide projection may also include an outer edge intermediate the superior surface and the inferior surface.

In some embodiments of the retractor, the outer edge may include a convex surface.

In some embodiments of the retractor, the distal end of the arcuate projection may include a first tip, a second tip, and a recess intermediate the first tip and the second tip. At least one of the first tip, the second tip, and the recess may be shaped to guide a medial collateral ligament toward the retractor surface as the retractor member is inserted into a knee joint.

In some embodiments, the retractor may also include a handle connection feature disposed at the proximal end of the retractor shaft.

In some embodiments, the retractor shaft may also include a first shaft portion extending along the first longitudinal axis, a second shaft portion extending along a second longitudinal axis, and a third shaft portion extending along a third longitudinal axis. The second shaft portion may be located intermediate the first shaft portion and the second shaft portion, and the third shaft portion may be offset from the first shaft portion.

According to some embodiments, a method for retracting a medial collateral ligament with an assembly including a retractor and a retractor handle is provided. In some embodiments, the retractor may include a handle connection feature and an arcuate projection having a convex retractor surface and a cutting shield surface. In some embodiments, the retractor handle may include a retractor connection feature configured to engage the handle connection feature to removably couple the retractor handle with the retractor. The method may include coupling the retractor handle to the retractor by engaging the retractor connection feature with the handle connection feature, inserting the retractor into an incision at a surgical site proximal a knee joint, maneuvering the retractor relative to the knee joint, and placing the retractor on a lateral side of a medial collateral ligament of the knee joint.

In some embodiments, the method may also include retracting the medial collateral ligament away from a tibial plateau of the knee joint with the convex retractor surface.

In some embodiments, the method may also include resecting at least a portion of the tibial plateau with a bone saw while retracting the medial collateral ligament away from the tibial plateau in order to prevent damaging the medial collateral ligament with the bone saw.

In some embodiments, the method may also include resecting at least a portion of a tibial plateau of the knee joint with a bone saw while the cutting shield surface prevents the bone saw from damaging the medial collateral ligament.

In some embodiments, the method may also include translating the retractor connection feature between a locked position and an unlocked position to removably couple the retractor handle with the retractor.

In some embodiments of the method, in the locked position the retractor connection feature may be engaged with the handle connection feature to lock the retractor handle to the retractor, and in an unlocked position the retractor connection feature may be disengaged with the handle connection feature to unlock the retractor handle from the retractor.

These and other features and advantages of the present disclosure will become more fully apparent from the following description and appended claims, or may be learned by the practice of the instruments, systems, and methods set forth hereinafter.

BRIEF DESCRIPTION OF THE DRAWINGS

Exemplary embodiments of the disclosure will become more fully apparent from the following description and appended claims, taken in conjunction with the accompanying drawings. Understanding that these drawings depict only exemplary embodiments and are, therefore, not to be considered limiting of the scope of the appended claims, the exemplary embodiments of the present disclosure will be described with additional specificity and detail through use of the accompanying drawings in which:

Figures 1A, 1B:
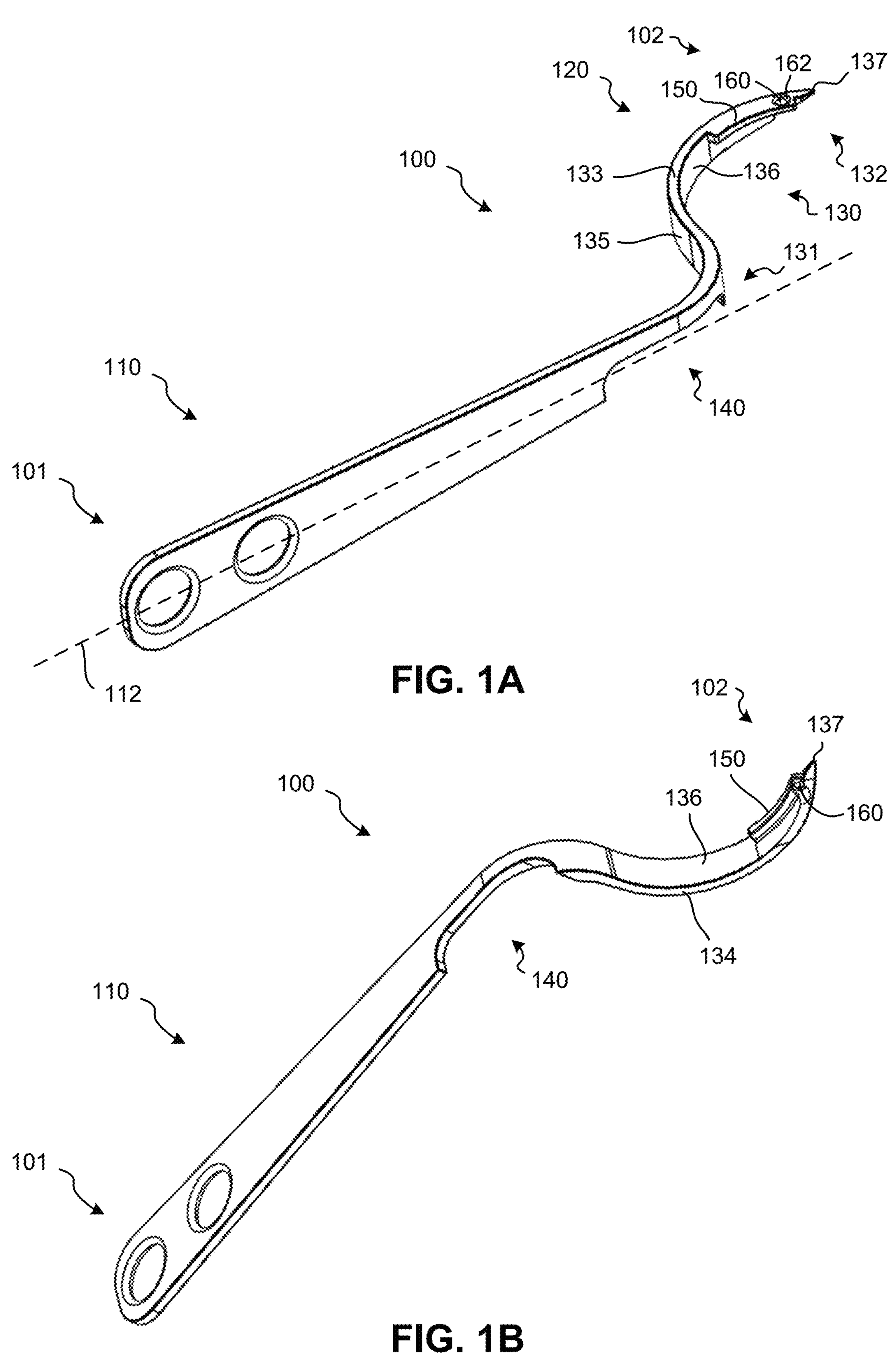
FIG. 1A is a perspective view of a retractor, according to an embodiment of the present disclosure.
FIG. 1B is another perspective view of the retractor of FIG. 1A.
Figures 1C, 1D:
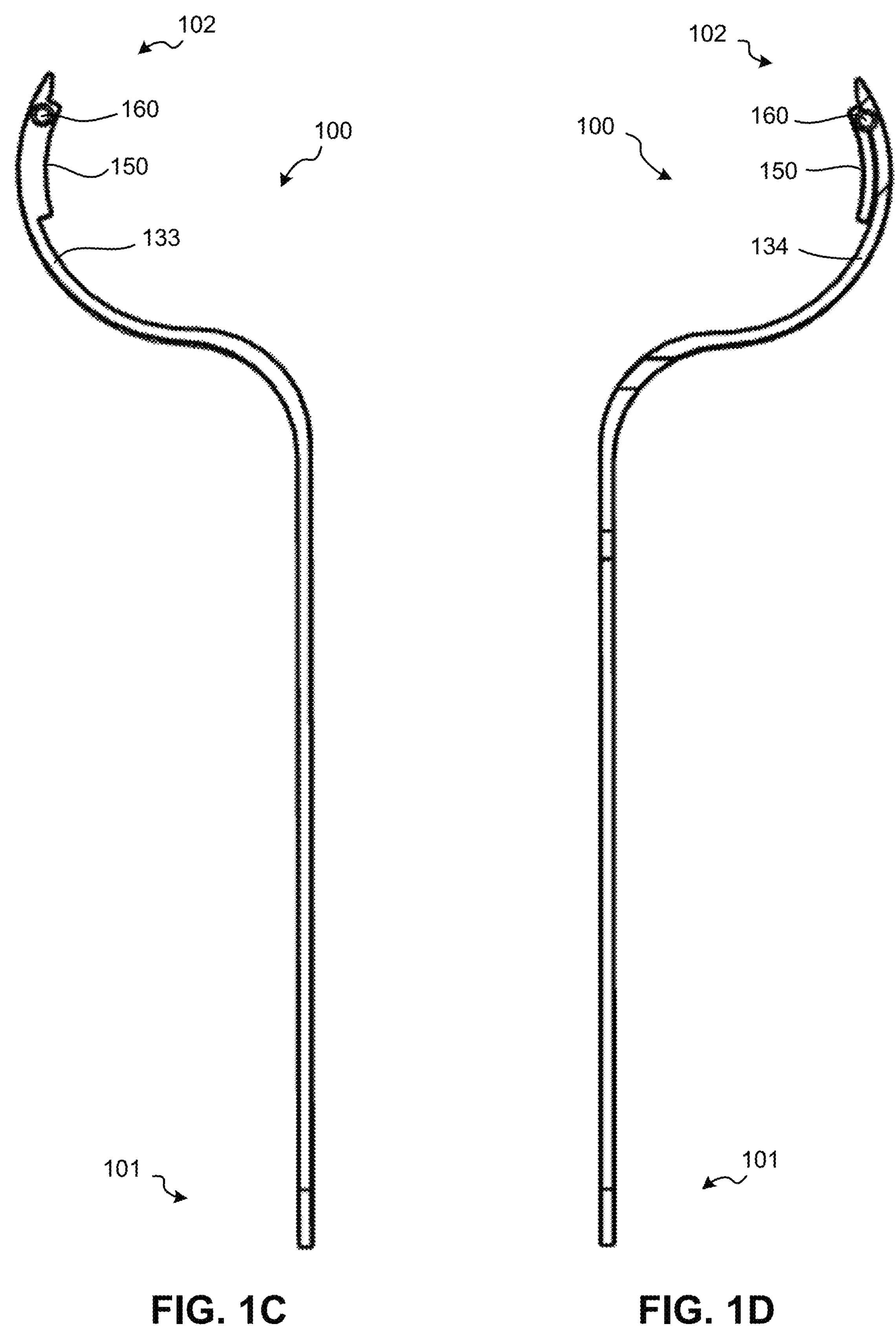
FIG. 1C is a top view of the retractor of FIG. 1A.
FIG. 1D is a bottom view of the retractor of FIG. 1A.

It is to be understood that the drawings are for purposes of illustrating the concepts of the disclosure and may not be drawn to scale. Furthermore, the drawings illustrate exemplary embodiments and do not represent limitations to the scope of the present disclosure.

DETAILED DESCRIPTION

Exemplary embodiments of the present disclosure will be best understood by reference to the drawings, wherein like parts are designated by like numerals throughout. It will be readily understood that the components of the present disclosure, as generally described and illustrated in the Figures herein, could be arranged and designed in a wide variety of different configurations. Thus, the following more detailed description of the embodiments of the apparatus, systems, and method, as represented in the Figures, is not intended to limit the scope of the present disclosure, as claimed in this or any other application claiming priority to this application, but is merely representative of exemplary embodiments of the present disclosure.

Standard medical directions, planes of reference, and descriptive terminology are employed in this specification. For example, anterior means toward the front of the body. Posterior means toward the back of the body. Superior, or caudal, means toward the head. Inferior, or cephalad, means toward the feet. Medial means toward the midline of the body. Lateral means away from the midline of the body. Axial means toward a central axis of the body. Abaxial means away from a central axis of the body. Ipsilateral means on the same side of the body. Contralateral means on the opposite side of the body. A sagittal plane divides a body into right and left portions. A midsagittal plane divides the body into bilaterally symmetric right and left halves. A coronal plane divides a body into anterior and posterior portions. A transverse plane divides a body into superior and inferior portions. These descriptive terms may be applied to an animate or inanimate body.

FIGS. 1A-I illustrate various views of a retractor 100, according to an embodiment of the present disclosure. The retractor 100 may include a proximal end 101, a distal end 102, a retractor handle 110 at the proximal end 101, and a retractor member 120 at the distal end 102 which may be coupled to the retractor handle 110.

The retractor handle 110 may extend or generally extend along a first longitudinal axis 112, as shown in FIG. 1A. However, it will be understood that the retractor handle 110 or portions of the retractor handle 110 may or may not extend along the first longitudinal axis 112 in a straight line. For example, the phrase "generally extend along an axis" may include straight or curved members that may or may not maintain a close proximity to an axis.

The retractor member 120 may include a generally arcuate projection, or arcuate projection 130, and a retractor coupling feature (e.g., such as a guide projection 150 having an attachment aperture 160, as one non-limiting example, which will be discussed in more detail below).

As defined herein, the term "generally arcuate" means having a curved shape, an arc shape, a "bow-like" shape, etc. The term "generally arcuate" can include curved shapes that are mathematically defined by a single radius along a given curved shape, as well as curved shapes that are mathematically defined by a plurality of radii along a given curved shape. However, it will also be understood that the term "generally arcuate" may or may not include curved shapes that are defined by one or more precise mathematical formulas. Moreover, "generally arcuate" may not only include curved shapes that extend along a curvilinear pathway, but also shapes consisting of a series of rectilinear segments that combine to define larger scale curvatures or curved shapes. Thus, for example, a geodesic dome may be said to have a spherical curvature even though the spherical shape is defined by planar segments.

The arcuate projection 130 may transversely project away from the first longitudinal axis 112. The arcuate projection 130 may include a proximal end 131 (which may be coupled to the retractor handle 110 and/or coupled to a notch 140 formed intermediate the retractor handle 110 and the retractor member 120), a distal end 132, a superior surface 133, and an inferior surface 134. The arcuate projection 130 may also include a retractor surface 135 that extends intermediate the superior surface 133 and the inferior surface 134. In some embodiments, the retractor surface 135 may have a convex curvature. The arcuate projection 130 may further include a cutting shield surface 136, opposite the retractor surface 135, which may extend intermediate the superior surface 133 and the inferior surface 134. In some embodiments, the cutting shield surface 136 may have a concave curvature.

Figures 1E, 1F:
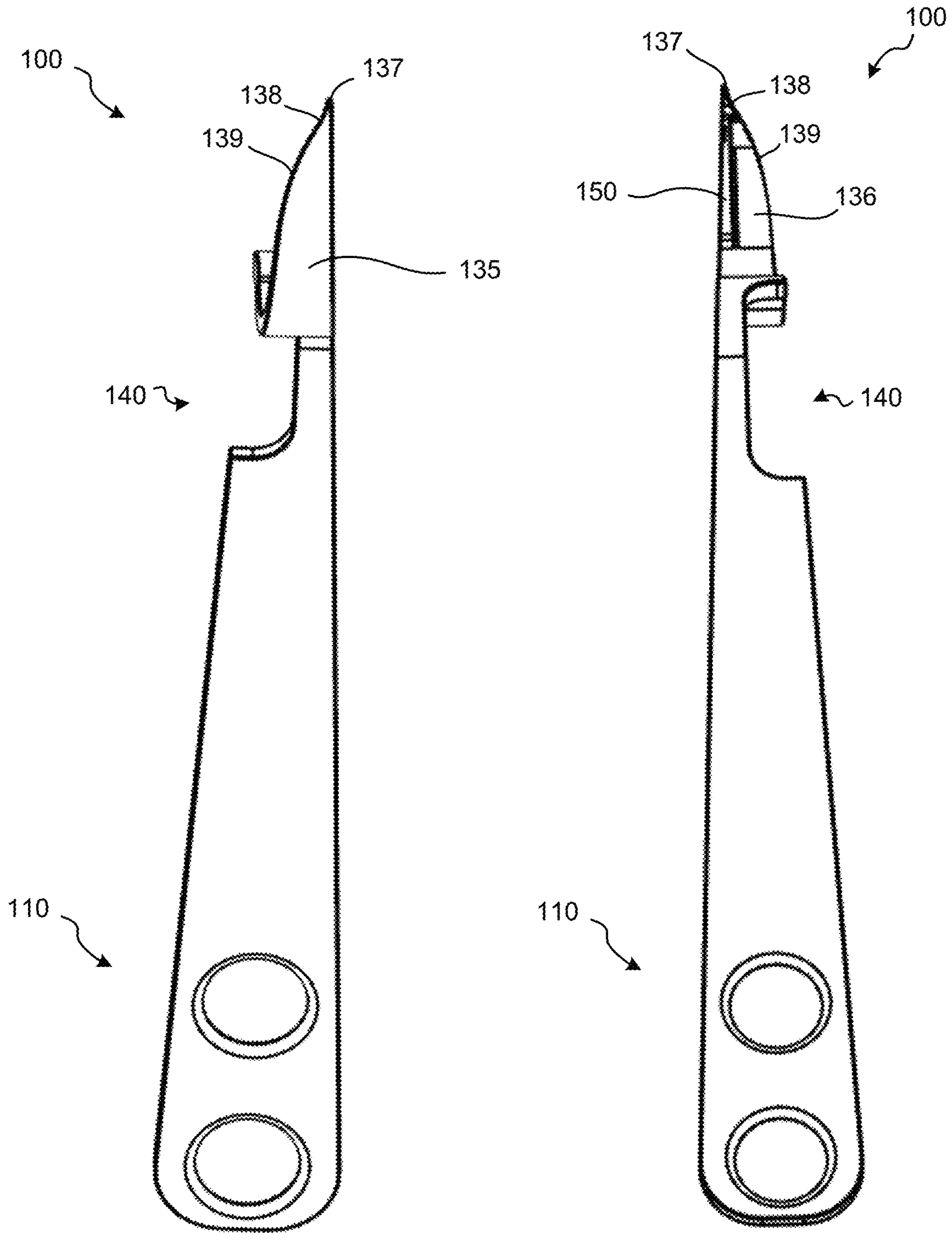
FIG. 1E is a left side view of the retractor of FIG. 1A.
FIG. 1F is a right side view of the retractor of FIG. 1A.
Figures 1G, 1H, 1I:
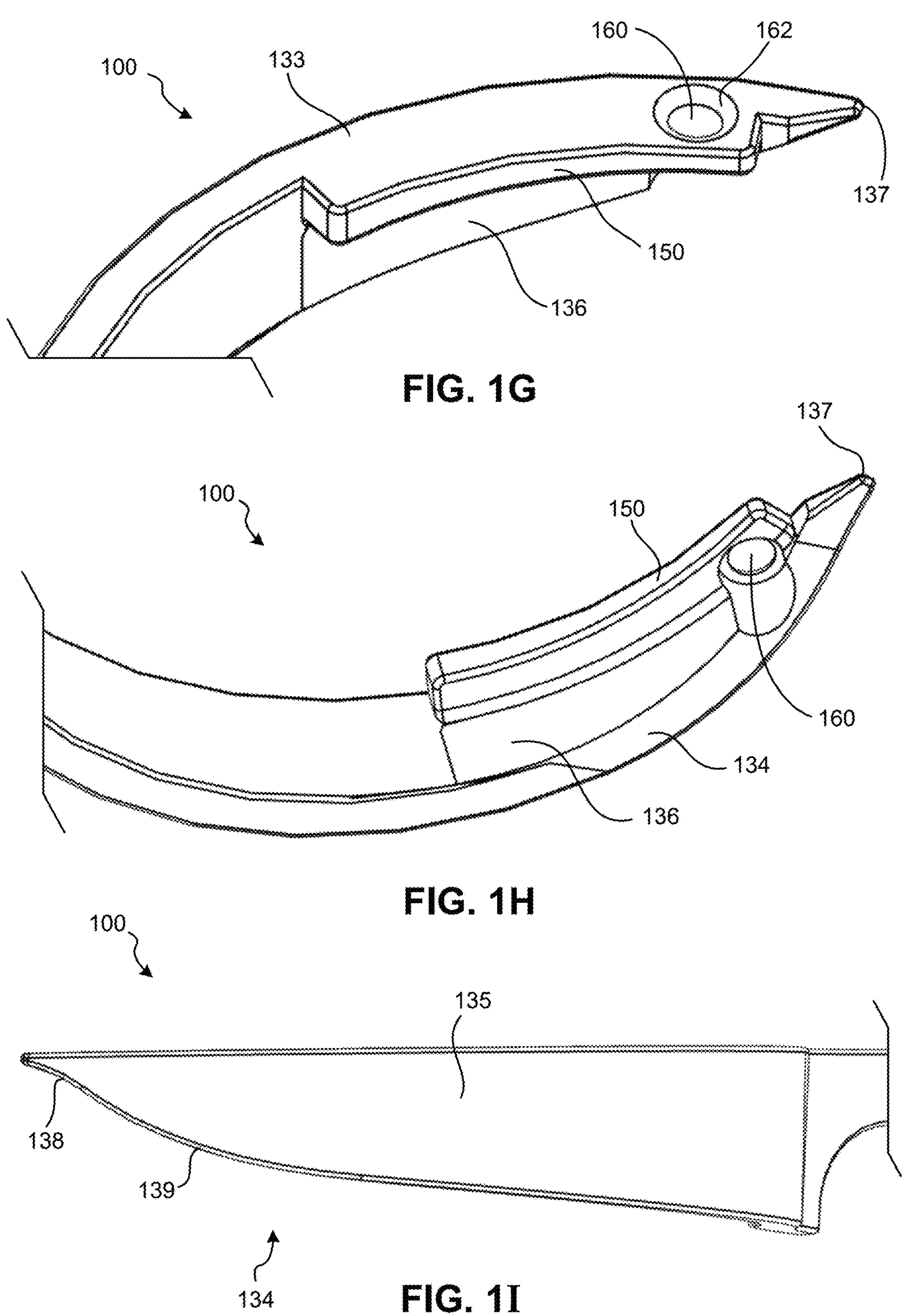
FIG. 1G is a perspective top view of the distal end of the retractor of FIG. 1A.
FIG. 1H is a perspective bottom view of the distal end of the retractor of FIG. 1A.
FIG. 1I is a left side view of the distal end of the retractor of FIG. 1A.

The distal end 132 of the arcuate projection 130 may include a pointed tip 137. The distal end 132 of the arcuate projection 130 near the pointed tip 137 may also include a lower concave curvature 138 and a lower convex curvature 139 that may be formed in the inferior surface 134 of the arcuate projection 130, as shown in FIGS. 1E, 1F, and 1I. Each of the pointed tip 137, the concave curvature 138, and/or the convex curvature 139, may help facilitate maneuvering of the distal end 102 of the retractor 100 within a tight knee joint during a surgical procedure. Moreover, in some embodiments the retractor surface 135 and the cutting shield surface 136 of the arcuate projection 130 may both decrease in height moving from the proximal end 131 of the arcuate projection 130 toward the distal end 132 of the arcuate projection 130 to further aid maneuvering of the distal end 102 of the retractor 100 within a tight knee joint, as can be seen in FIG. 1I.

In some embodiments, the retractor coupling feature may comprise a guide projection 150. The guide projection 150 may be coupled to the cutting shield surface 136 of the arcuate projection 130 and may project toward the first longitudinal axis 112. The guide projection 150 may be configured to rest on top of a tibial plateau during a knee joint arthroplasty procedure in order to help properly place the retractor 100 during a tibial plateau resection, as will be discussed in more detail below. The guide projection 150 may also include an attachment aperture 160 formed in, or through, the guide projection 150. The attachment aperture 160 may also include a chamfered surface 162, as will be discussed in more detail below.

Figures 2A, 2B:
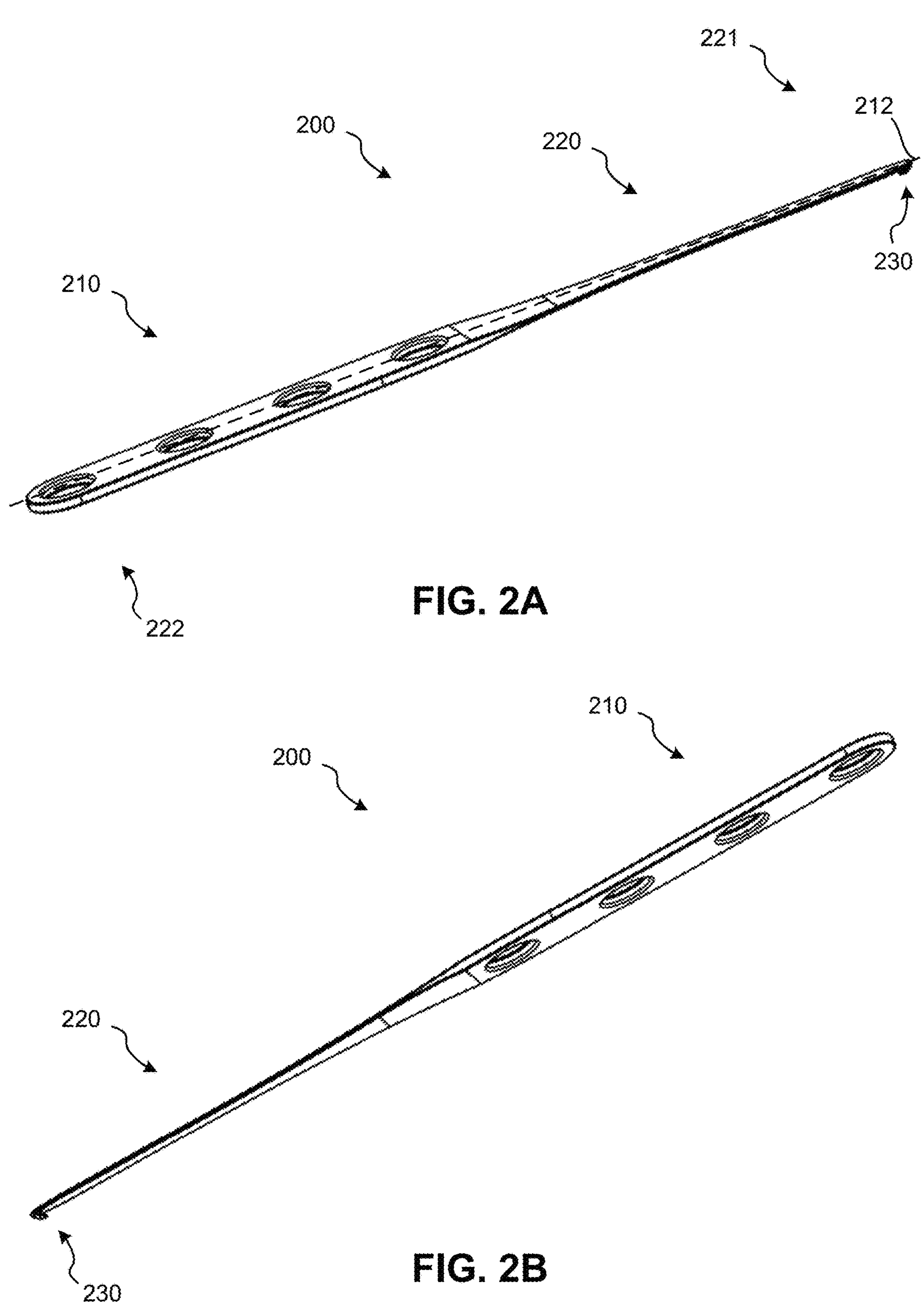
FIG. 2A is a perspective view of a guide rod, according to an embodiment of the present disclosure.
FIG. 2B is another perspective view of the guide rod of FIG. 2A.
Figure 2C:
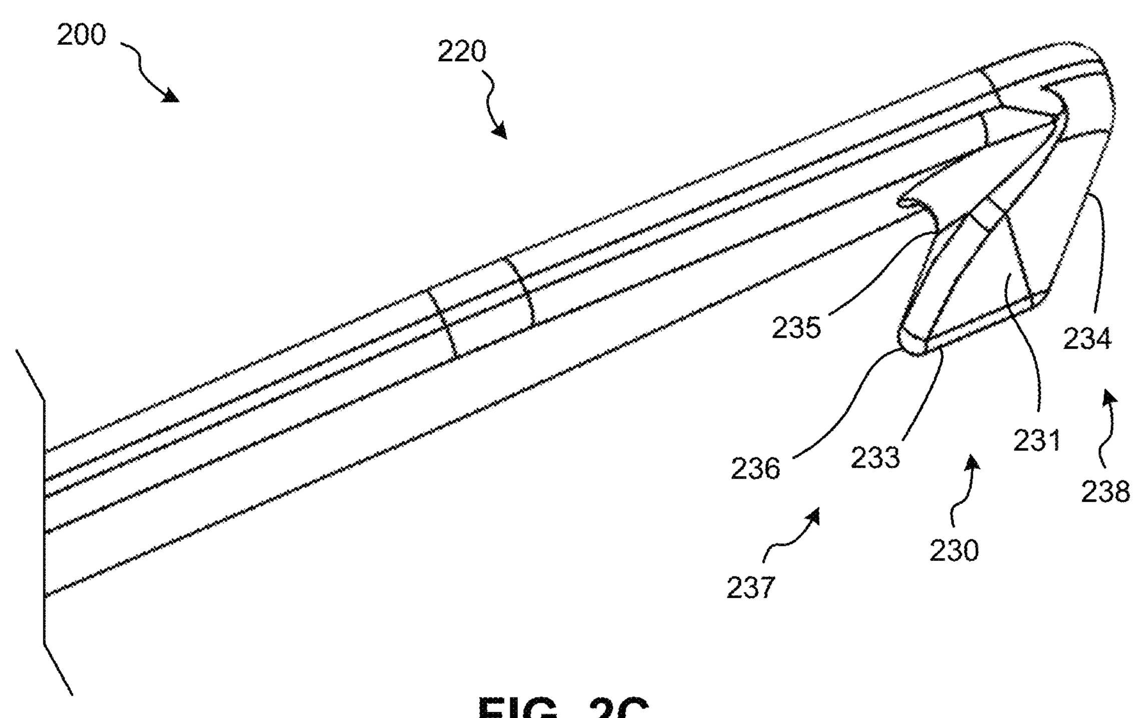
FIG. 2C is a perspective bottom view of the distal end of the guide rod of FIG. 2A.
Figure 2C:
Figure 2D:
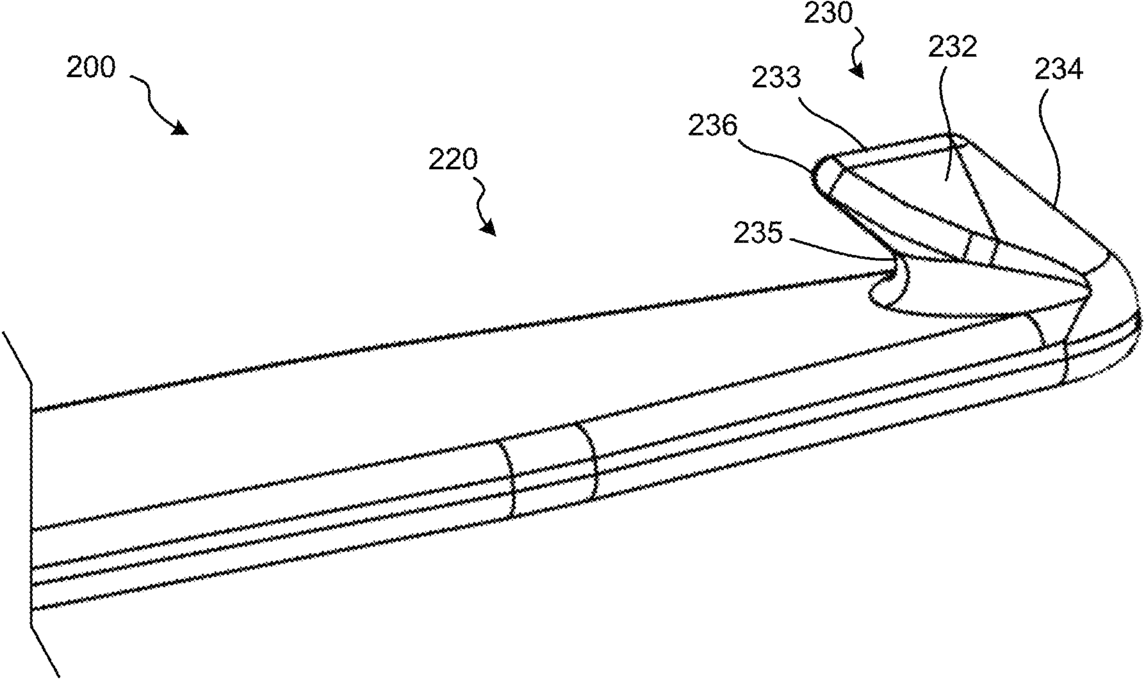
FIG. 2D is another perspective bottom view of the distal end of the guide rod of FIG. 2A.
Figure 2E:
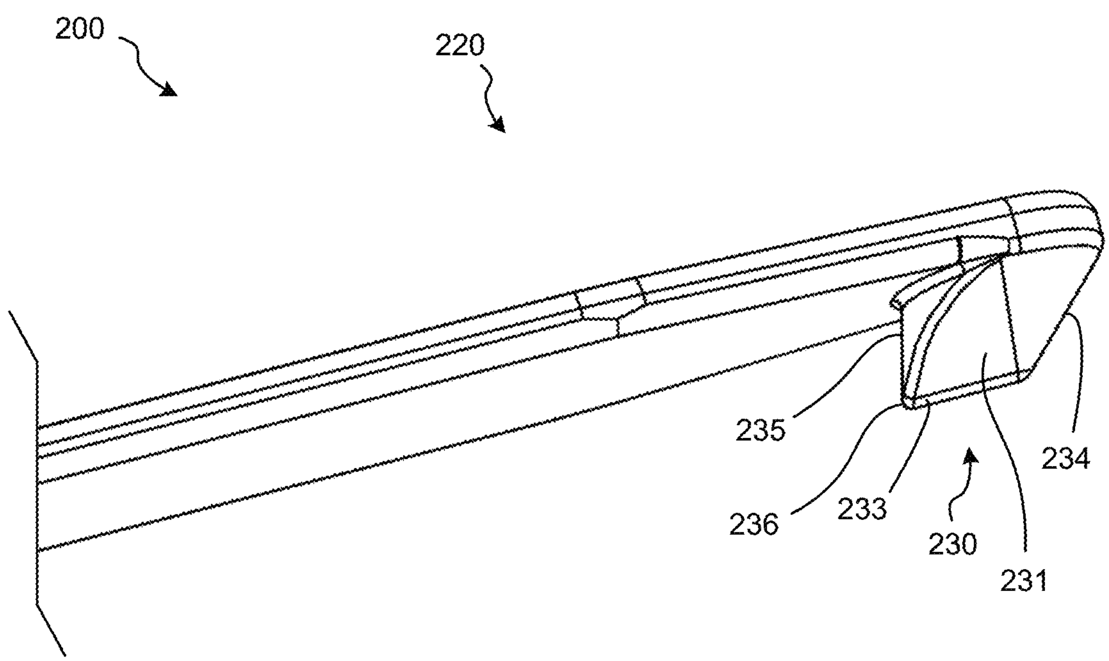
FIG. 2E is a perspective bottom view of the distal end of the guide rod of FIG. 2A with an alternative hook member shape.
Figure 2F:
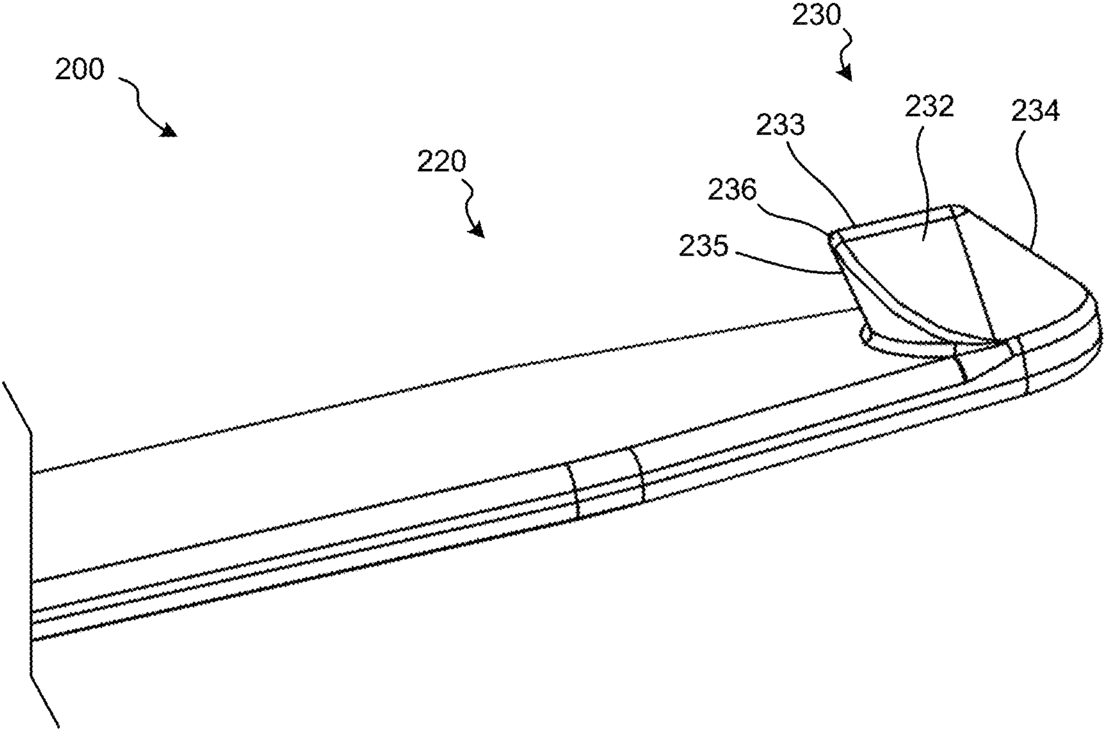
FIG. 2F is another perspective bottom view of the distal end of the guide rod of FIG. 2E.
Figures 2G, 2H:
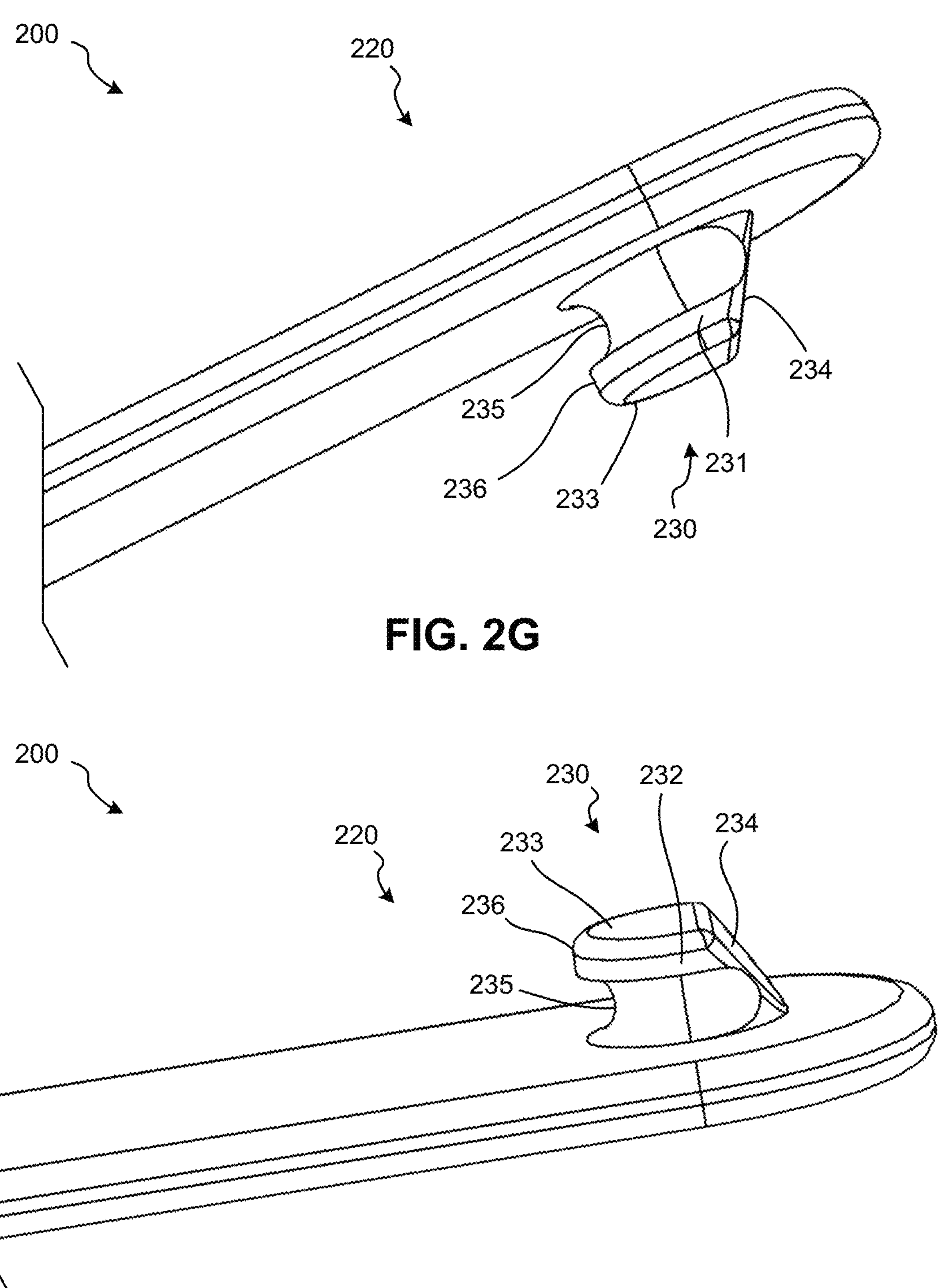
FIG. 2G is a perspective bottom view of the distal end of the guide rod of FIG. 2A with an alternative shape and hook member design.
FIG. 2H is another perspective bottom view of the distal end of the guide rod of FIG. 2H.

FIGS. 2A-2H illustrate various views of a guide rod 200, according to embodiments of the present disclosure. The guide rod 200 may include a guide rod handle 210 and an elongate member 220 that may be coupled to the guide rod handle 210 and/or integrally formed therewith. The elongate member 220 may include a proximal end, or rod proximal end 222, and a rod coupling feature (e.g., such as a hook member 230, as one non-limiting example, which will be discussed below in more detail) that may be coupled to a distal end, or rod distal end 221, of the elongate member 220. The guide rod handle 210 and/or the elongate member 220 may extend or generally extend a long a second longitudinal axis 212, as shown in FIG. 2A.

In some embodiments, the rod coupling feature of the guide rod 200 may be configured to engage the retractor coupling feature of the retractor 100 in order to pivotably couple the guide rod 200 to the retractor 100 and form an assembly 10, as will be discussed below in more detail with respect to FIGS. 3-6.

Although specific example structures for the retractor coupling feature and the rod coupling feature are presented herein, it will be understood that these are mere exemplary structures given for illustration purposes only. Accordingly, any suitable shape, form, structure, feature, etc., is contemplated herein that can form a retractor coupling feature and/or a corresponding rod coupling feature that may engage with each other to pivotably couple the guide rod 200 to the retractor 100, without departing from the spirit or scope of the present disclosure.

In some embodiments, the rod coupling feature may comprise a hook member 230. The hook member 230 may transversely project away from the elongate member 220 and/or the second longitudinal axis 212. The hook member 230 may be shaped to be received within the attachment aperture 160 formed in the guide projection 150 of the retractor 100 in order to pivotably couple the guide rod 200 to the retractor 100. The hook member 230 may assume any suitable shape in order to pivotably couple the guide rod 200 to the retractor 100. FIGS. 2C-2H illustrate three non-limiting examples of hook members 230 having different shapes that may be configured to pivotably couple the guide rod 200 to the retractor 100. However, it will also be understood that any number of differently shaped hook members that can pivotably couple the guide rod 200 to the retractor 100 are envisioned herein. The hook member 230 may include a first side 231, a second side 232, a superior side 233, a distal hook surface 234, a proximal hook surface 235, and a hook member tip 236.

In some embodiments, the proximal hook surface 235 may extend about a proximal end 237 of the hook member 230 from the first side 231 to the second side 232.

In some embodiments, at least a portion of the proximal hook surface 235 may extend toward the guide rod handle 210, or rod proximal end 222, at a first angle. The shape and/or angle of the proximal hook surface 235 may be selected to facilitate pivotable coupling of the guide rod 200 to the retractor 100.

In some embodiments, the hook member tip 236 may extend or project toward the rod proximal end 222 above at least a portion of the proximal hook surface 235.

In some embodiments, at least a portion of the proximal hook surface 235 may comprise a cam surface configured to interact with a surface associated with the attachment aperture 160.

In some embodiments, at least a portion of the proximal hook surface 235 may be concave.

In some embodiments, at least a portion of the proximal hook surface 235 may be convex.

In some embodiments, at least a portion of the distal hook surface 234 may extend or generally extend toward the guide rod handle 210, or rod proximal end 222, at a second angle.

In some embodiments, the shape and/or second angle of the distal hook surface 234 on a distal end 238 of the hook member 230 may be selected to engage the chamfered surface 162 of the attachment aperture 160 in order to facilitate decoupling of the guide rod 200 from the retractor 100 when a distally directed force of sufficient magnitude is applied to the guide rod 200 relative to the retractor 100.

In some embodiments, the first side 231 and the second side 232 may angle together towards the superior side 233 of the hook member 230.

Figure 3:
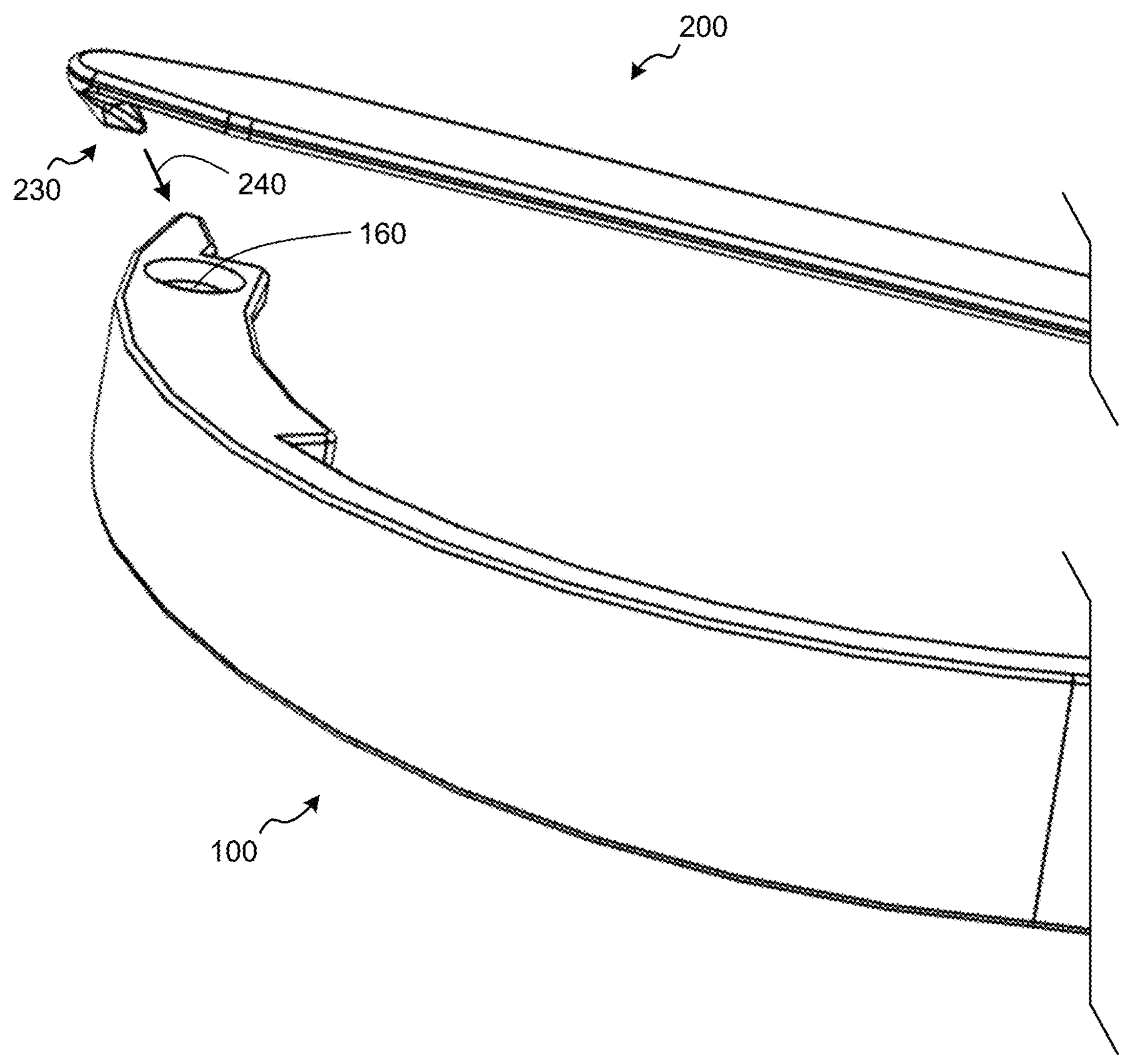
FIG. 3 is a perspective view of the distal end of the retractor of FIG. 1A and the distal end of the guide rod of FIG. 2A, prior to assembly.

FIG. 3 is a perspective view of the distal ends of the retractor 100 and guide rod 200 before they are assembled together. A surgeon may assemble the retractor 100 and the guide rod 200 together by inserting the hook member 230 into the attachment aperture 160 in the direction of arrow 240 shown in FIG. 3.

Figures 4, 5:
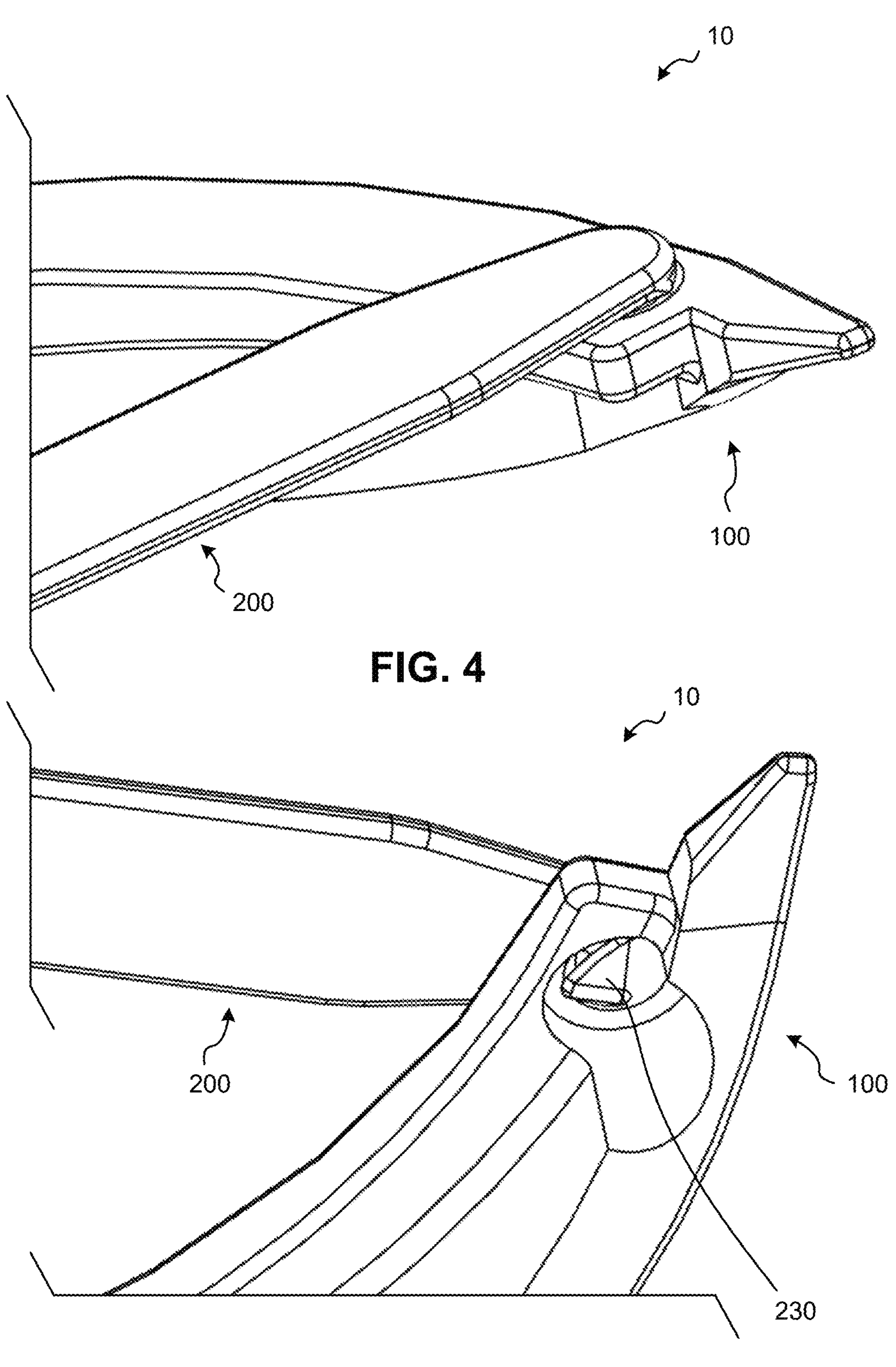
FIG. 4 is a perspective top view of the distal ends of the retractor and guide rod shown in of FIG. 3, after assembly.
FIG. 5 is a perspective bottom view of the distal ends of the retractor and guide rod shown in of FIG. 3, after assembly.
Figure 6:
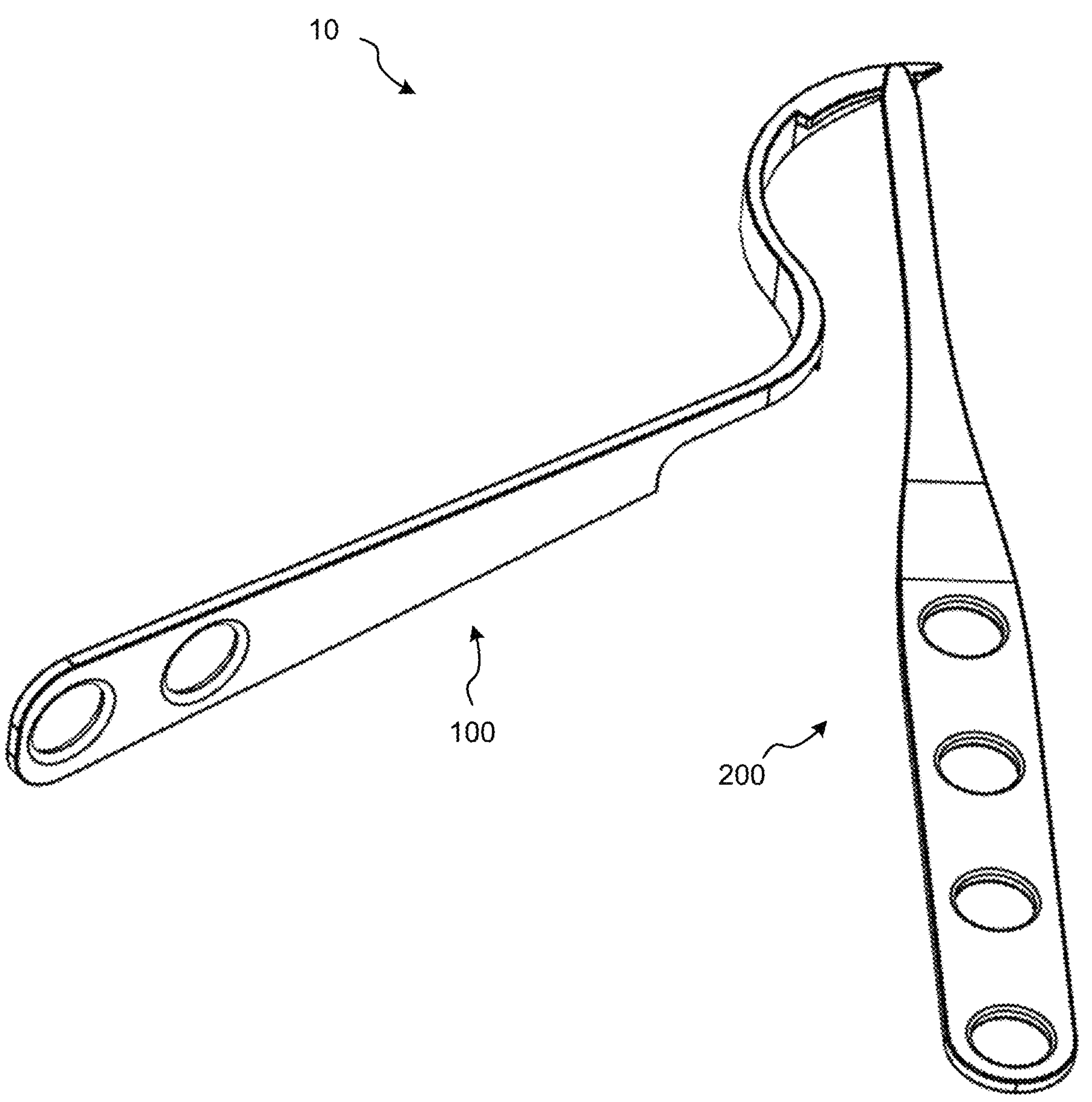
FIG. 6 is a perspective view of the entire assembly of FIGS. 4 and 5.

FIGS. 4-6 illustrate various perspective views of the retractor 100 and guide rod 200 after they have been assembled together to form an assembly 10. As previously discussed, the guide rod 200 may be decoupled from the retractor 100 by applying a distally directed force of sufficient magnitude to the guide rod 200. This will cause the distal hook surface 234 (which may be angled as discussed above) to engage the chamfered surface 162 that surrounds the attachment aperture 160 (which may also be angled in a complementary fashion to the distal hook surface 234) in order to decouple the guide rod 200 from the retractor 100.

Figure 7:
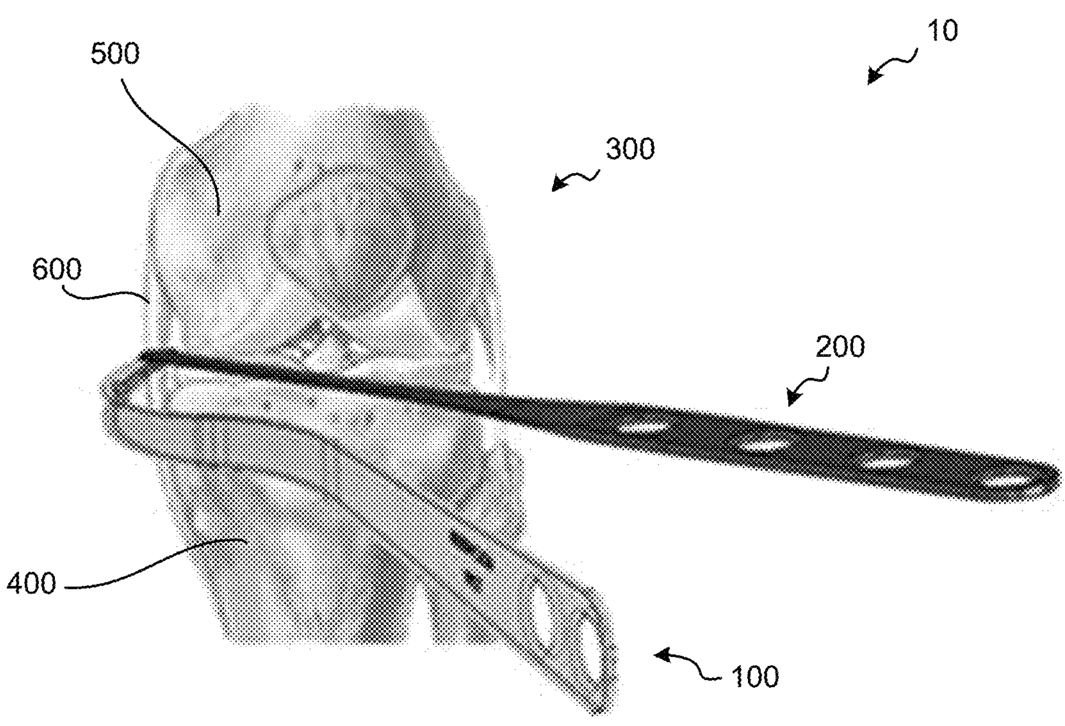
FIG. 7 is a perspective view of the assembly of FIG. 6 inserted into a knee joint during a surgical procedure.

FIG. 7 is a perspective view of the assembly 10 inserted into a knee joint 300 during a surgical procedure. The knee joint 300 may include a tibia 400, a femur 500, and a medial collateral ligament 600. The guide rod 200, pivotably coupled to the retractor 100, helps prevent the distal end of the retractor 100 from being accidentally placed on the medial side of the medial collateral ligament 600 during insertion of the by the surgeon. Rather, the guide rod 200 will help ensure that the distal end of the retractor 100 will be placed on the lateral side of the medial collateral ligament 600 by the surgeon during insertion. Once the distal end of the retractor 100 has been properly positioned on the lateral side of the medial collateral ligament 600, the guide rod 200 may be decoupled from the retractor 100 (as previously discussed) and removed from the knee joint 300.

Figure 8:
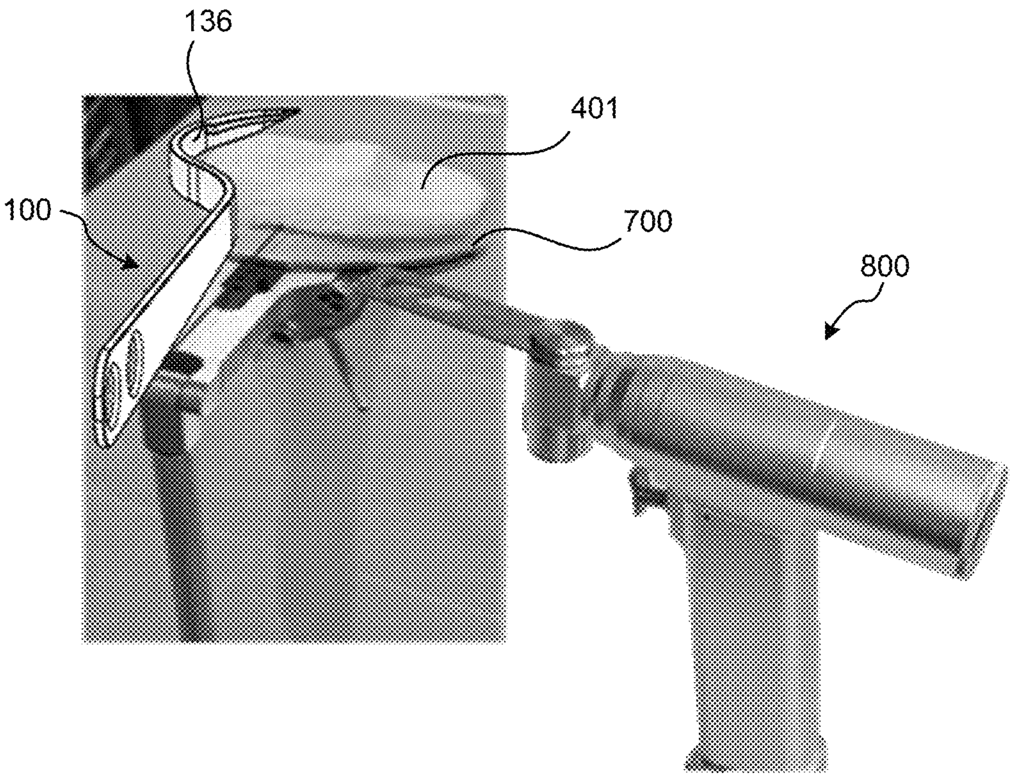
FIG. 8 is a perspective view of the retractor of FIG. 1A relative to a tibia, cutting guide, and bone saw during a tibial plateau resection procedure.

FIG. 8 is a perspective view of the retractor 100, a tibia 401, a cutting guide 700 engaged with the tibia 401, and a bone saw 800, in preparation for a tibial plateau resection procedure. The retractor 100 may be utilized by a surgeon to retract a medial collateral ligament of the knee joint (not shown in FIG. 8) away from the tibial plateau during the resection procedure. The cutting shield surface 136 of the retractor 100 may also act as a mechanical stop to the blade of the bone saw 800 to further protect the medial collateral ligament from accidental damage or cutting during the tibial plateau resection procedure.

Figure 9:
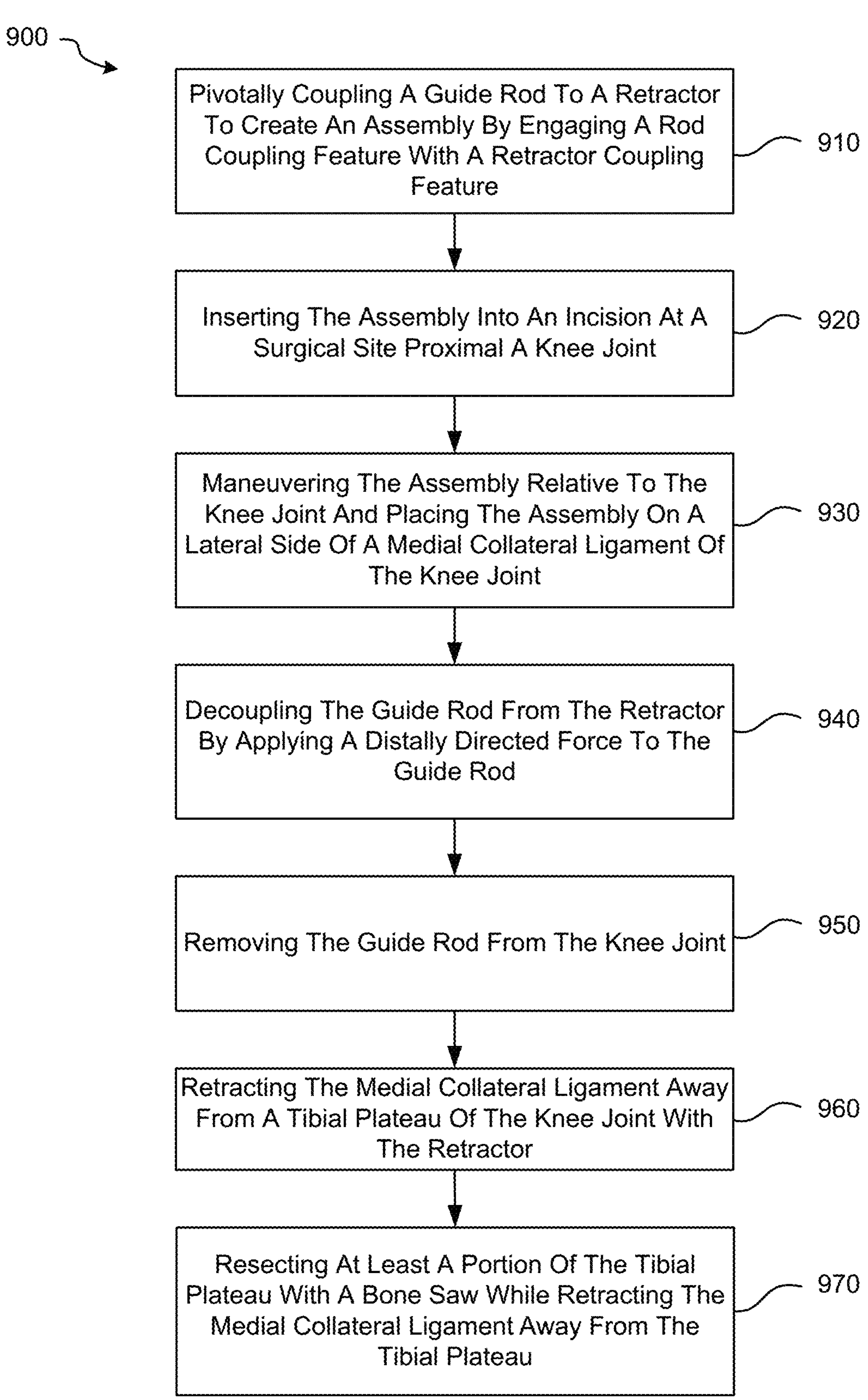
FIG. 9 is a flowchart of a method for retracting a medial collateral ligament with an assembly during a knee joint arthroplasty procedure.

FIG. 9 is a flowchart of a method 900 for retracting a medial collateral ligament with an assembly 10 during a knee joint arthroplasty procedure. The assembly 10 may include a retractor 100 having a retractor coupling feature and a guide rod 200 having a rod coupling feature configured to engage the retractor coupling feature to pivotably couple the guide rod 200 to the retractor 100.

The method 900 may begin with a step 910 in which the guide rod 200 may be pivotally coupled to the retractor 100 to create the assembly 10 by engaging the rod coupling feature with the retractor coupling feature. In some embodiments, this may be accomplished by inserting a hook member 230 of the guide rod 200 into an attachment aperture 160 formed in the distal end of the retractor 100.

Once the guide rod 200 has been coupled to the retractor 100, the method 900 may proceed to a step 920 in which the assembly 10 may be inserted into an incision (not shown) at a surgical site proximal a knee joint.

Once the assembly 10 has been inserted into the incision, the method 900 may proceed to a step 930 in which the assembly 10 may be maneuvered relative to the knee joint in order to place the assembly 10 on a lateral side of a medical collateral ligament of the knee joint. The guide rod 200, coupled to the retractor 100, can ensure the retractor 100 does not end up on the medial side of the medical collateral ligament, as previously discussed.

Alternatively, or in addition thereto, once the assembly 10 has been placed on the lateral side of the medical collateral ligament, the method 900 may proceed to a step 940 in which the guide rod 200 may be decoupled from the retractor 100 by applying a distal force to the guide rod 200 relative to the retractor 100, as previously discussed. The decoupled guide rod 200 may then be removed from the knee joint in a step 950.

Once the guide rod 200 has been decoupled from the retractor 100 and removed from the knee joint, the method 900 may proceed to a step 960 in which the surgeon may utilize the retractor 100 to retract the medial collateral ligament away from a tibial plateau of the knee joint.

Alternatively, or in addition thereto, the method 900 may proceed to a step 970 in which a portion of the tibial plateau may be resected with a bone saw while the medial collateral ligament is retracted away from the tibia, and the method 900 may end.

In this manner, the medial collateral ligament may be protected from damage by the bone saw during the resection procedure. The retractor 100 may protect the medial collateral ligament in at least two ways including: (1) via retraction, which increases a separation distance between the bone saw blade and the medial collateral ligament, thus decreasing the likelihood of damaging the medial collateral ligament; and (2) the cutting shield surface 136 of the retractor 100 may directly shield the medial collateral ligament from the bone saw blade to prevent the bone saw blade from damaging the medial collateral ligament. Thus, the cutting shield surface 136 can help in all instances where the separation distance achieved from retraction may or may not be sufficient to keep the medial collateral ligament away from the bone saw blade.

Figure 10:
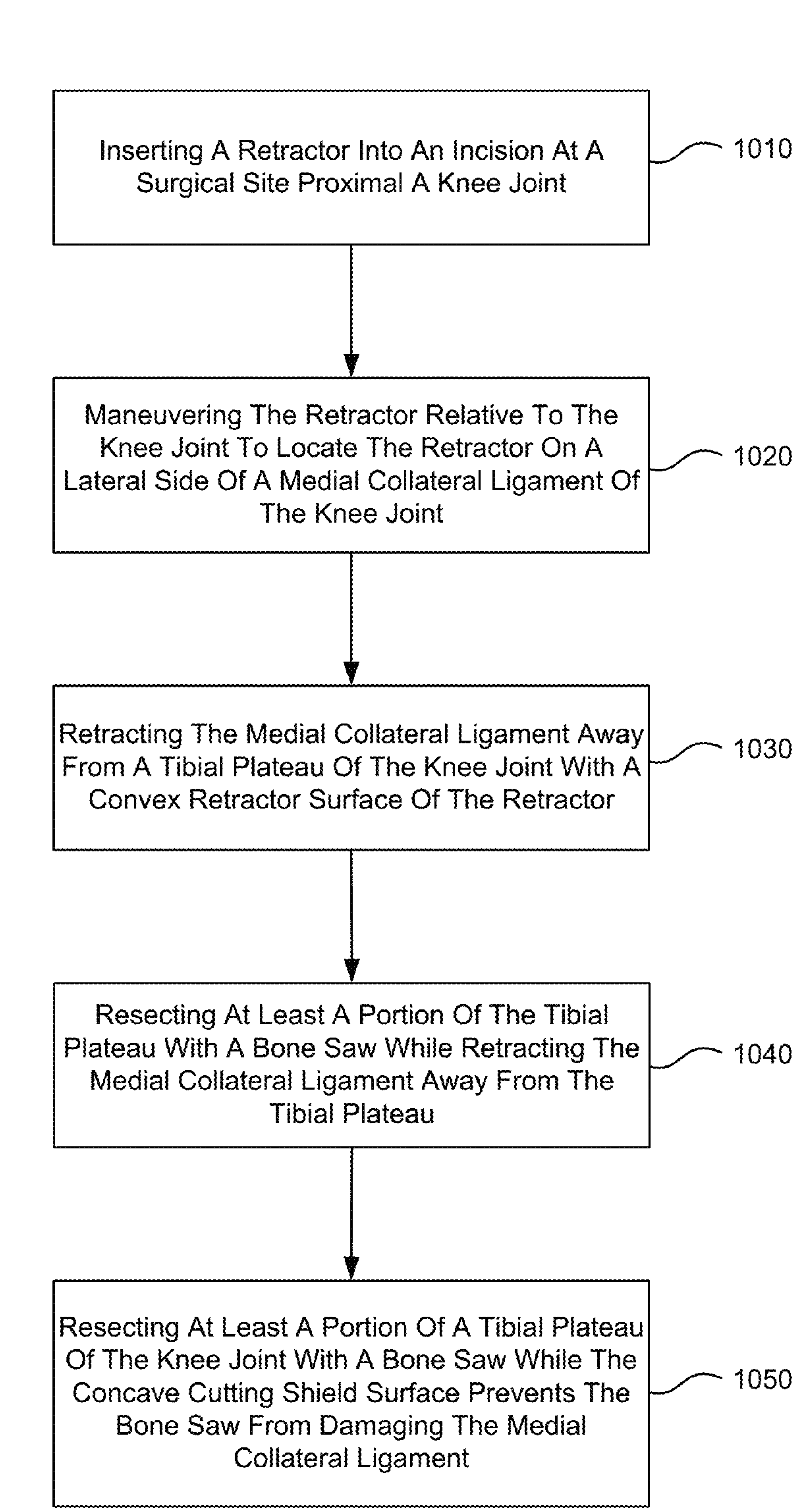
FIG. 10 is a flowchart of a method for retracting a medial collateral ligament with a retractor during a knee joint arthroplasty procedure.

FIG. 10 is a flowchart of a method 1000 for retracting a medial collateral ligament of a knee joint with a retractor 100. In some embodiments, the retractor 100 may include an arcuate projection having a retractor surface 135 that may be convex and a cutting shield surface 136 that may be concave.

The method 1000 may begin with a step 1010 in which the retractor 100 may be inserted into an incision (not shown) at a surgical site proximal the knee joint.

Once the retractor 100 has been inserted into the incision, the method 1000 may proceed to a step 1020 in which the retractor 100 may be maneuvered relative to the knee joint in order to locate the retractor 100 on a lateral side of the medical collateral ligament.

Once the retractor 100 has been located on the lateral side of the medical collateral ligament, the method 1000 may proceed to a step 1030 in which the surgeon may utilize the retractor surface 135 of the retractor 100 to retract the medial collateral ligament away from a tibial plateau of the knee joint.

Alternatively, or in addition thereto, the method 1000 may proceed to a step 1040 in which a portion of the tibial plateau may be resected with a bone saw while the medial collateral ligament is retracted away from the tibia in order to prevent the bone saw from damaging the medial collateral ligament.

Alternatively, or in addition thereto, the method 1000 may proceed to a step 1050 in which a portion of the tibial plateau may be resected with a bone saw while the cutting shield surface 136 of the retractor 100 directly prevents the bone saw from damaging the medial collateral ligament, and the method 1000 may end.

Thus, as previously discussed, the medial collateral ligament may be protected from damage by the bone saw during the resection procedure. The retractor 100 may protect the medial collateral ligament including: (1) via retraction, which increases a separation distance between the bone saw blade and the medial collateral ligament, thus decreasing the likelihood of damaging the medial collateral ligament; and (2) the cutting shield surface 136 of the retractor 100 may directly shield the medial collateral ligament from the bone saw blade to prevent the bone saw blade from damaging the medial collateral ligament.

FIGS. 11A-11H illustrate various views of a retractor 1100, according to another embodiment of the present disclosure. The retractor 1100 may include a proximal end 1101, a distal end 1102, a retractor shaft or shaft 1110, a handle connection feature 1114 at the proximal end 1101 of the retractor 1100, and a retractor member 1120 at the distal end 1102 of the retractor 1100.

In some embodiments, the shaft 1110 may include a first shaft portion 1111, a second shaft portion 1112, and a third shaft portion 1113. In this manner, the third shaft portion 1113 may be offset from the first shaft portion 1111 to provide extra clearance and working space for the surgeon, as will be discussed in more detail below. The first shaft portion 1111 may extend or generally extend along a first longitudinal axis 1121, the second shaft portion 1112 may extend or generally extend along a second longitudinal axis 1122, and the third shaft portion 1113 may extend or generally extend along a third longitudinal axis 1123. However, it will be understood that any portion of the shaft 1110 may or may not extend along a particular longitudinal axis in a straight line and may generally include straight or curved members that may or may not maintain a close proximity to a particular longitudinal axis.

In some embodiments, the handle connection feature 1114 may be coupled to and/or extend proximally from the third shaft portion 1113.

In some embodiments, the handle connection feature 1114 may be configured to removably couple with a handle, as will be discussed in more detail below with respect to FIGS. 12A-D.

In some embodiments, the handle connection feature 1114 may comprise a hex key 1116, with a retention slot 1117 formed therein. However, it will be understood that the handle connection feature 1114 may comprise any conceivable shape or configuration to couple a handle to the handle connection feature 1114.

In some embodiments, the retractor 1100 may include an integrally formed handle (not shown) in lieu of the handle connection feature 1114.

In some embodiments, the retractor member 1120 may include a generally arcuate projection, or arcuate projection 1130, and a guide projection 1150.

The arcuate projection 1130 may transversely project away from the first longitudinal axis 1121. The arcuate projection 1130 may include a proximal end 1131 (which may be coupled to the first shaft portion 1111), a distal end 1132, a superior surface 1133, and an inferior surface 1134.

Figures 11A, 11B:
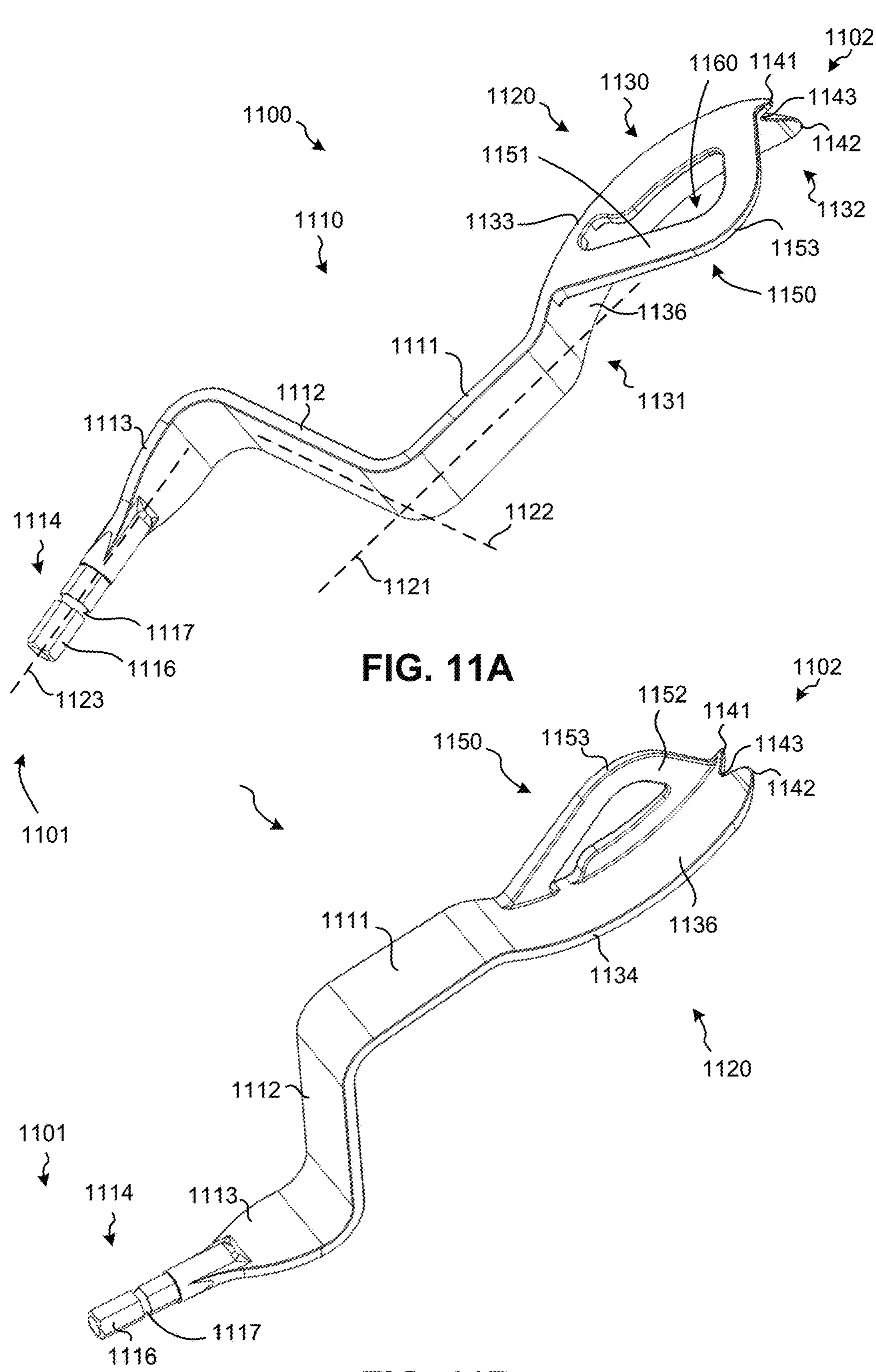
FIG. 11A is a top perspective view of a retractor, according to another embodiment of the present disclosure.
FIG. 11B is a bottom perspective view of the retractor of FIG. 11A.
Figure 11C:
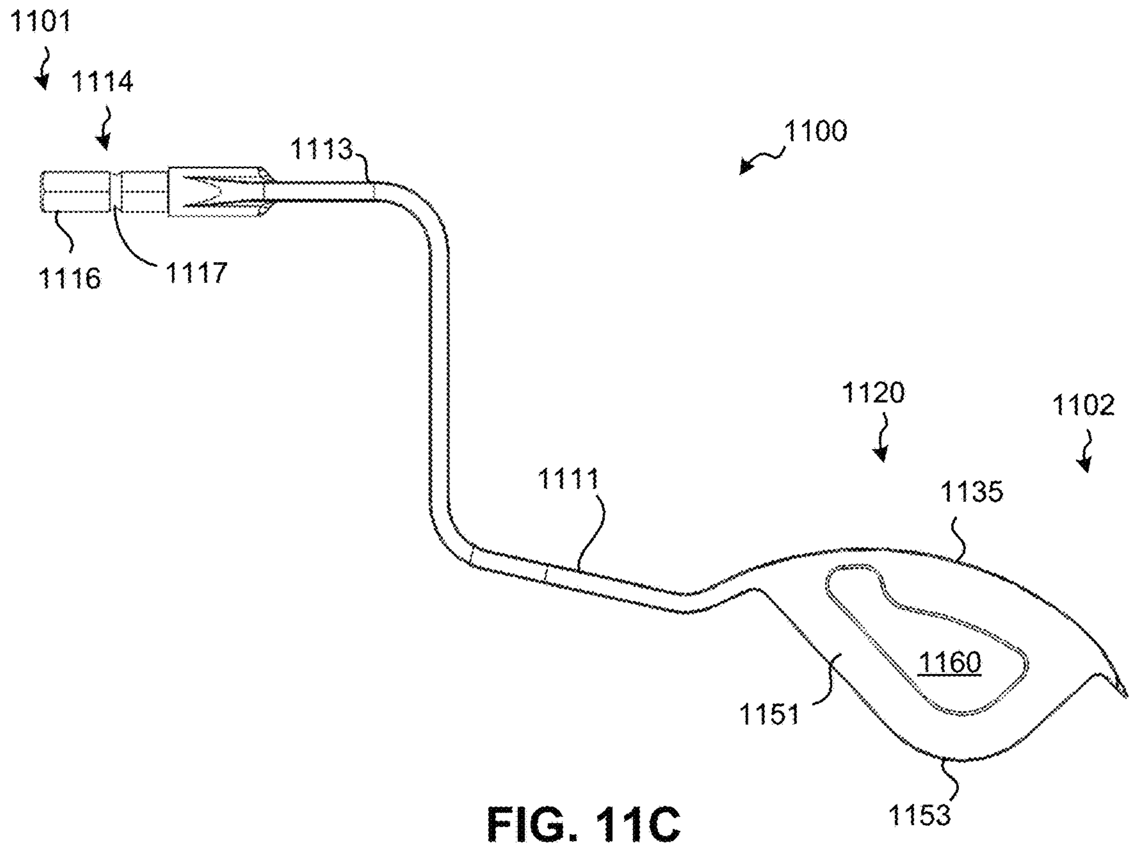
FIG. 11C is a top view of the retractor of FIG. 11A.
Figure 11D:
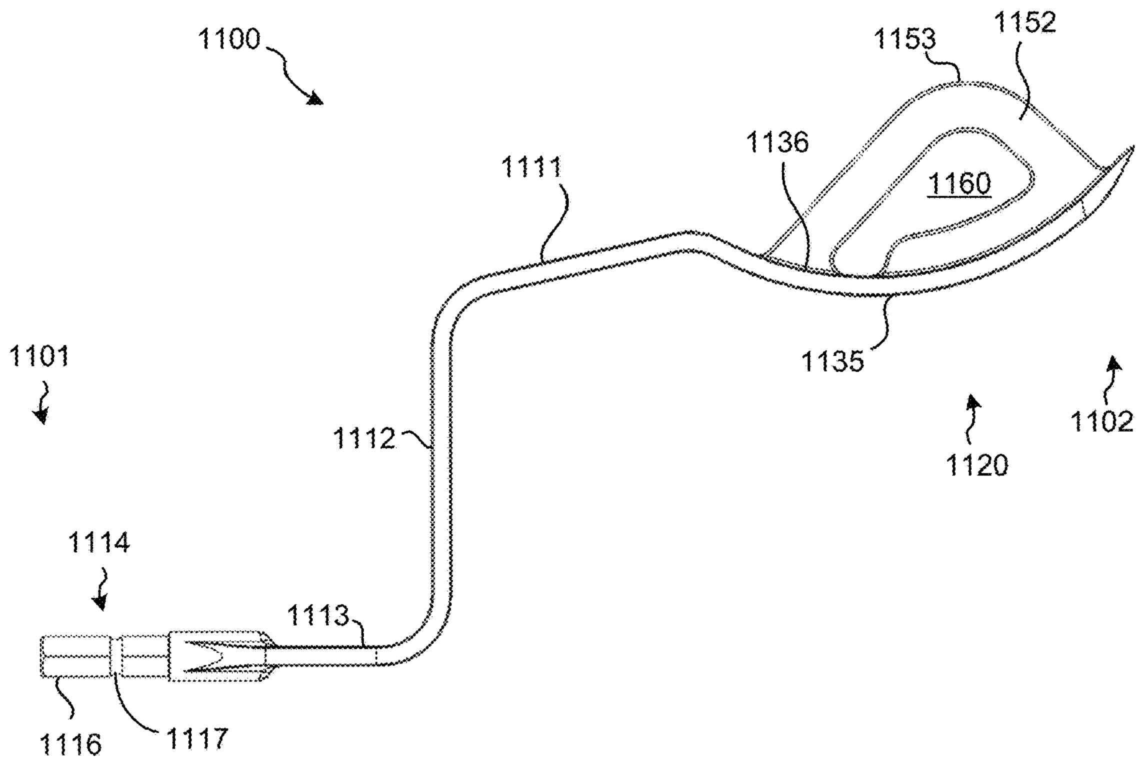
FIG. 11D is a bottom view of the retractor of FIG. 11A.
Figures 11E, 11F:
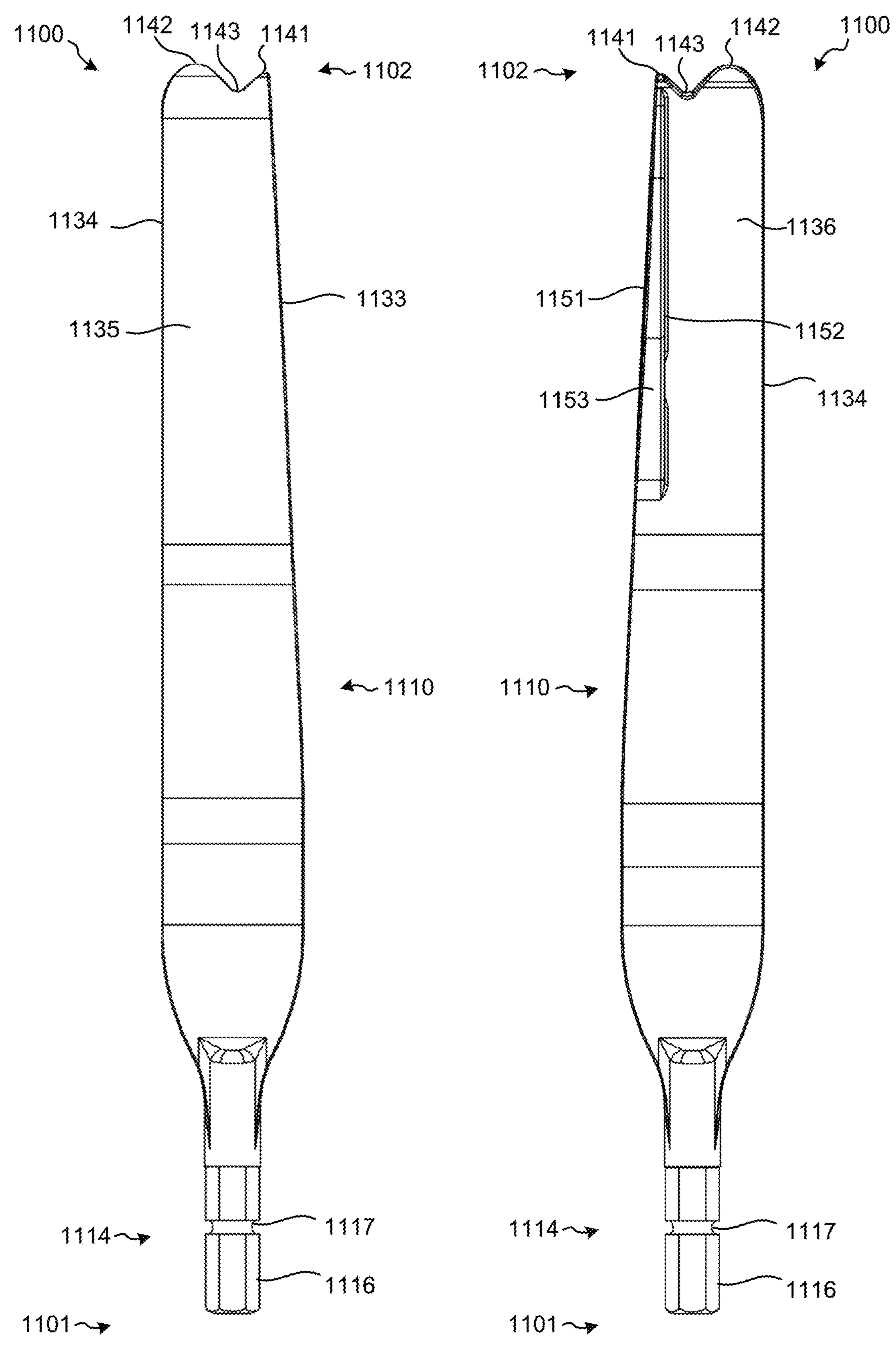
FIG. 11E is a left side view of the retractor of FIG. 11A.
FIG. 11F is a right side view of the retractor of FIG. 11A.
Figures 11G, 11H:
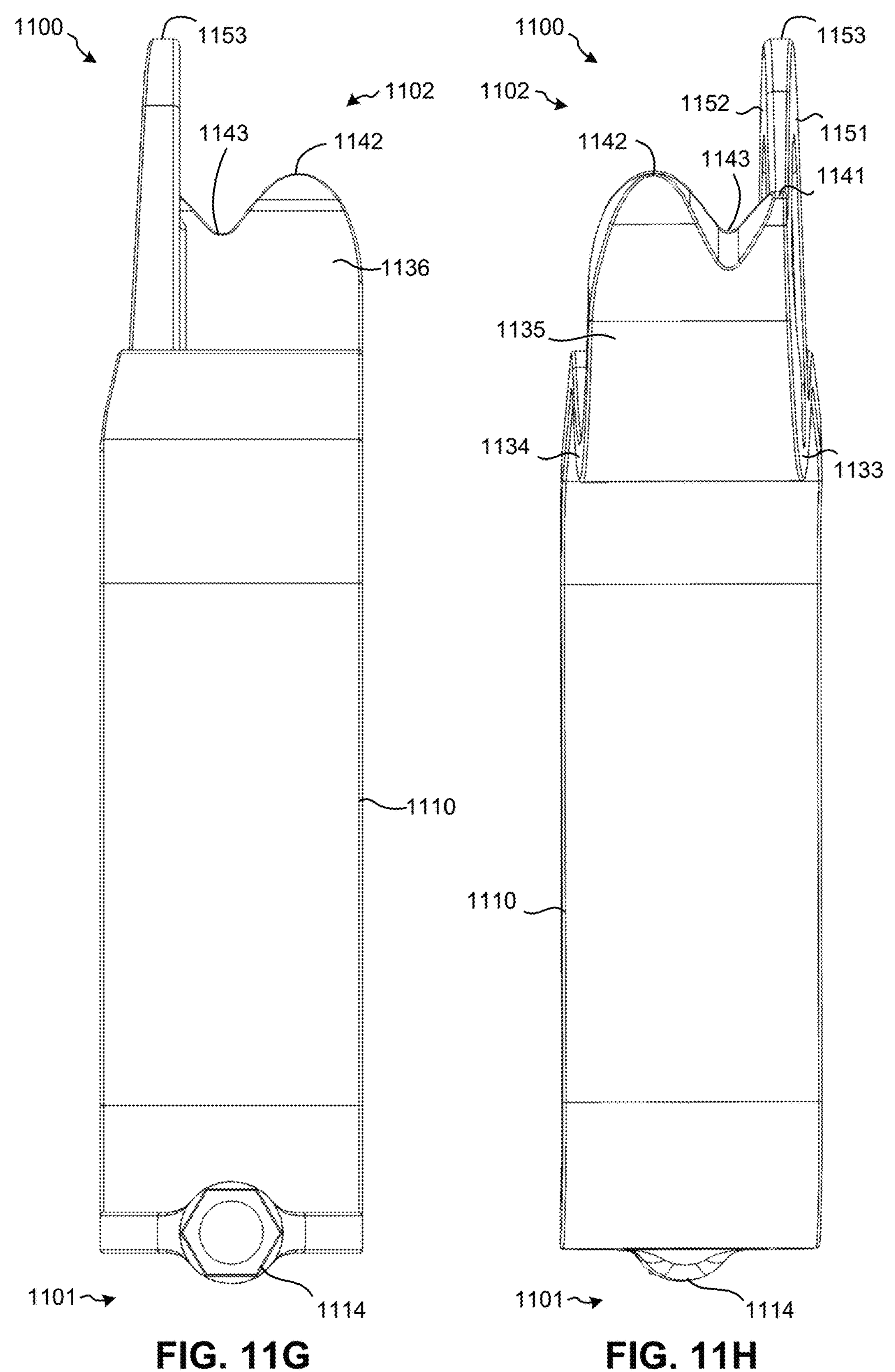
FIG. 11G is a proximal end view of the retractor of FIG. 11A.
FIG. 11H is a distal end view of the retractor of FIG. 11A.
Figure 12A:
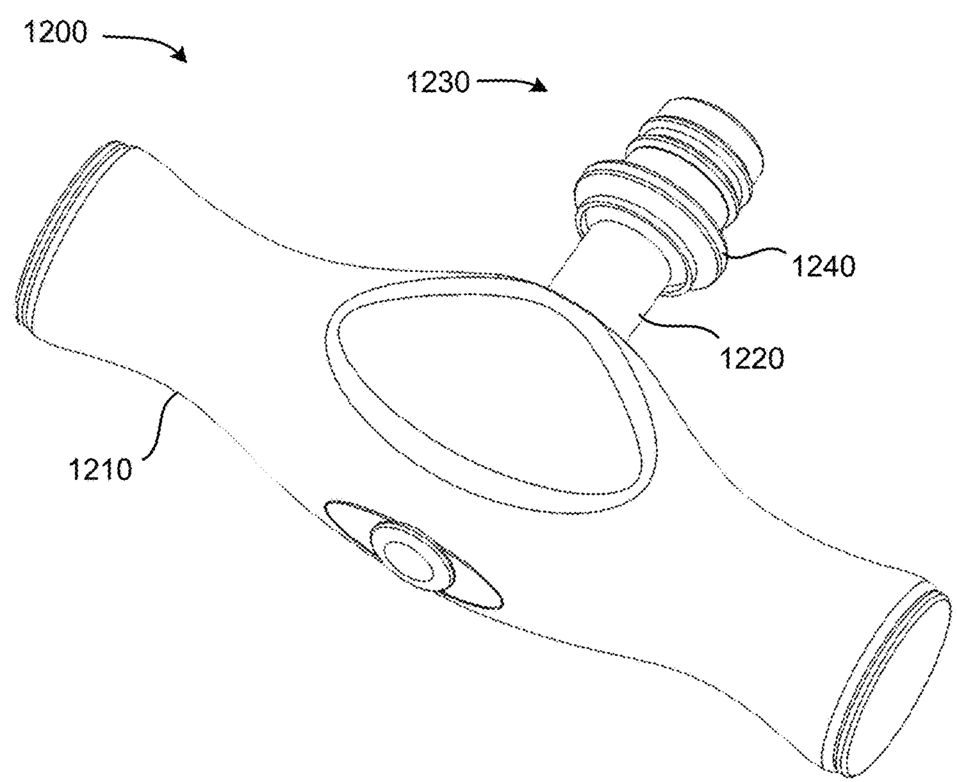
FIG. 12A is a perspective view of a handle, according to an embodiment of the present disclosure.
Figure 12B:
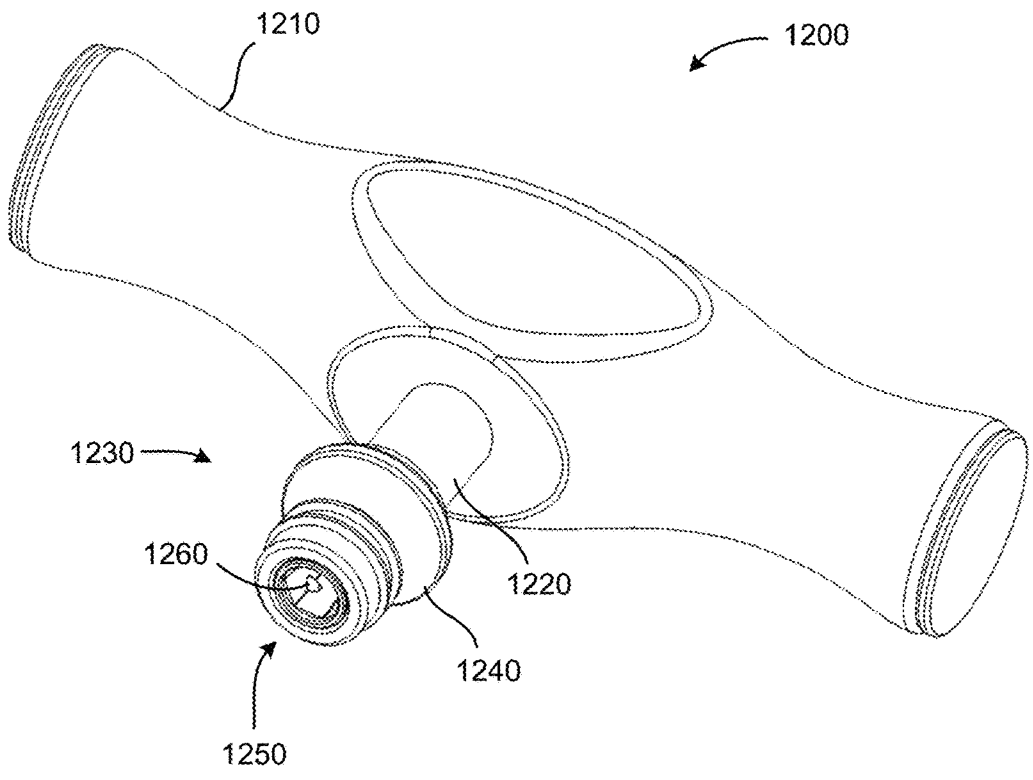
FIG. 12B is another perspective view of the handle of FIG. 12A.
Figure 12C:
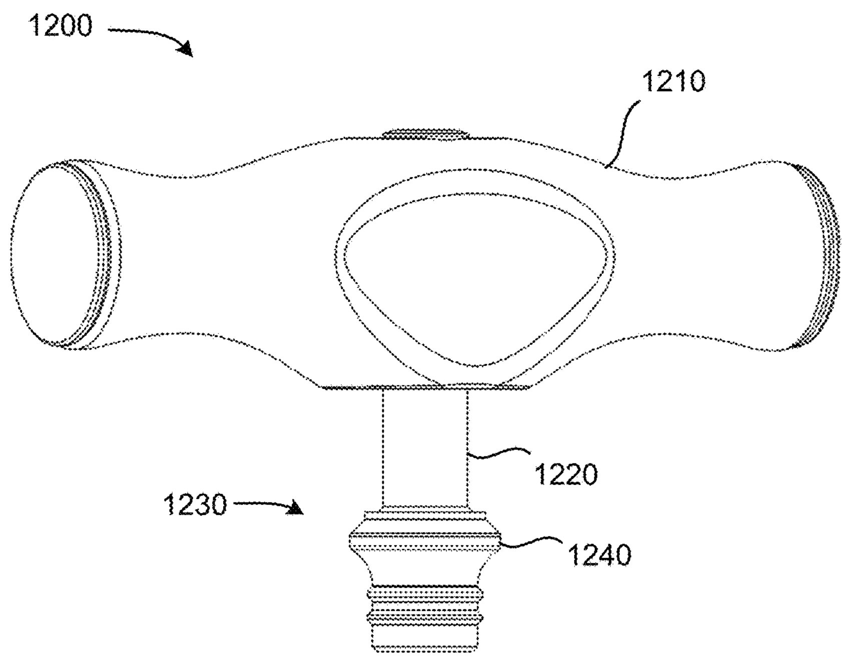
FIG. 12C is a side view of the handle of FIG. 12A.
Figure 12D:
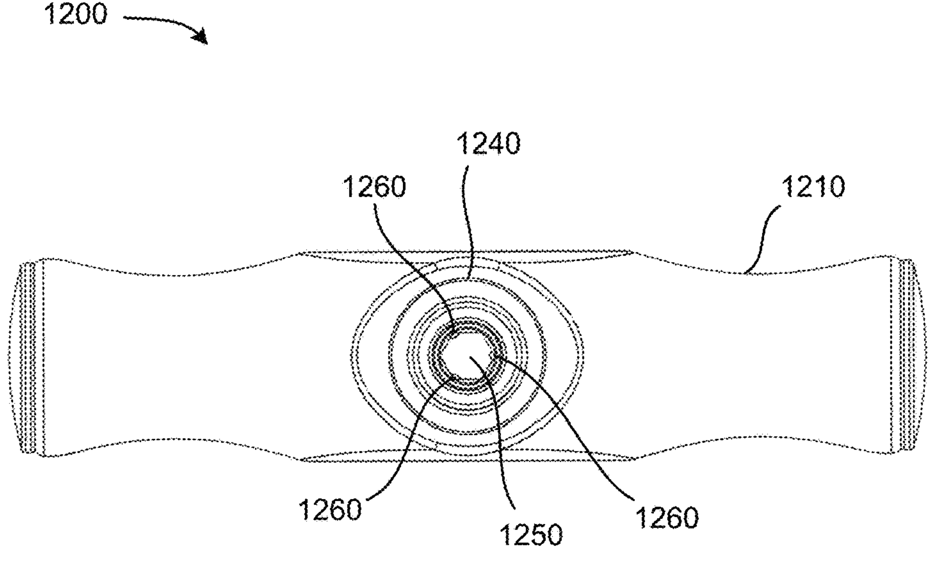
FIG. 12D is a distal end view of the handle of FIG. 12A.

In some embodiments, the superior surface 1133 and the inferior surface 1134 may taper toward each other moving from the proximal end 1131 of the arcuate projection 1130 toward the distal end 1132 of the arcuate projection 1130, as shown in FIG. 11H.

The arcuate projection 1130 may also include a retractor surface 1135 (see FIGS. 11E and 11H) that extends intermediate the superior surface 1133 and the inferior surface 1134. The retractor surface 1135 may have a convex curvature. The arcuate projection 1130 may further include a cutting shield surface 1136, opposite the retractor surface 1135, which may extend intermediate the superior surface 1133 and the inferior surface 1134. In some embodiments, the cutting shield surface 1136 may have a concave curvature.

In some embodiments, the distal end 1132 of the arcuate projection 1130 may include a first tip 1141 and a second tip 1142 separated by a recess 1143. At least one of the first tip 1141, the second tip 1142, and/or the recess 1143 may be tapered and/or otherwise shaped to guide a medial collateral ligament toward the retractor surface 1135 as the retractor member 1120 is inserted into a knee joint. Moreover, at least one of the first tip 1141, the second tip 1142, and/or the recess 1143 may be tapered and/or otherwise shaped to help separate tissue during insertion and/or facilitate maneuvering of the distal end 1102 of the retractor 1100 within a tight knee joint during a surgical procedure. In some embodiments, the retractor surface 1135 and the cutting shield surface 1136 of the arcuate projection 1130 may both decrease in height moving from the proximal end 1131 of the arcuate projection 1130 toward the distal end 1132 of the arcuate projection 1130 to further aid maneuvering of the distal end 1102 of the retractor 1100 within a tight knee joint, as can be seen in FIG. 11H.

The guide projection 1150 may include a superior surface 1151, an inferior surface 1152, and an outer edge 1153 intermediate the superior surface 1151 and the inferior surface 1152. The guide projection 1150 may be configured to rest on top of a tibial plateau during a knee joint arthroplasty procedure in order to help properly place the retractor 1100 during a tibial plateau resection (see FIGS. 13 and 14).

In some embodiments, the guide projection 1150 may be coupled to the cutting shield surface 1136 and project toward the first longitudinal axis 1121.

In some embodiments, the outer edge 1153 of the guide projection 1150 may include a convex surface.

In some embodiments, the superior surface 1151 and the inferior surface 1152 may taper toward each other moving from the proximal end 1131 of the arcuate projection 1130 toward the distal end 1132 of the arcuate projection 1130 (see FIG. 11F). This taper may help separate tissue and/or facilitate maneuvering of the distal end 1102 of the retractor 1100 within a tight knee joint during a surgical procedure.

In some embodiments, an aperture 1160 may be formed in or through the guide projection 1150.

Figure 13:
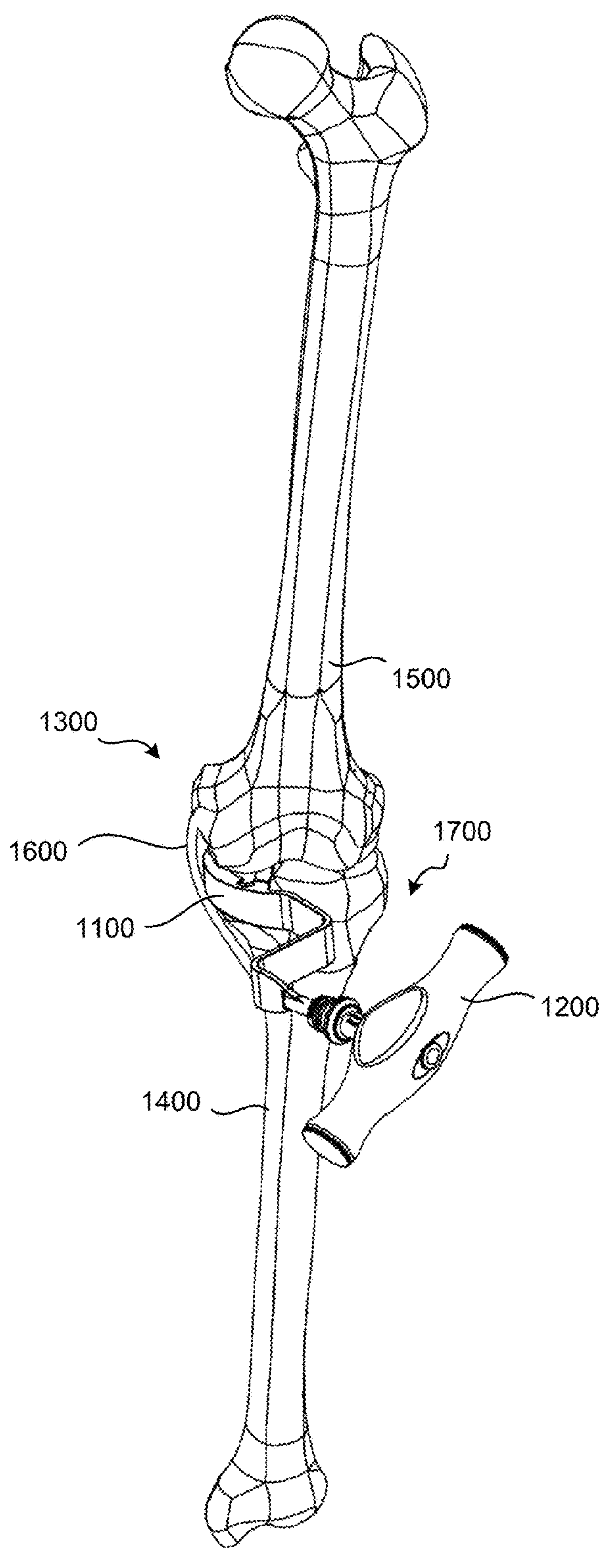
FIG. 13 is a perspective view of the retractor of FIG. 11A inserted into a knee joint during a surgical procedure.

In some embodiments, the aperture 1160 may be shaped to receive at least a portion of a femoral condyle therein to help locate, position, hold, and/or retain the retractor member 1120 relative to at least one of the femoral condyle and a tibial plateau of a knee joint during a surgical procedure (e.g., see FIG. 13).

In some embodiments, the retractor 1100 may be inserted into, positioned within, and/or removed from a knee joint without the use of an additional guide rod (such as the guide rod 200 described herein). However, it will also be understood that in other embodiments the retractor 1100 may be inserted into, positioned within, and/or removed from a knee joint with the use of an additional guide rod that may couple with the aperture 1160 via a suitable hook member (e.g., such as the guide rod 200 and hook member 230 described herein).

FIGS. 12A-D illustrate various views of a retractor handle, or handle 1200, according to an embodiment of the present disclosure. The handle 1200 may include a handle portion 1210, a handle shaft 1220, and a retractor connection feature 1230.

In some embodiments, the handle 1200 may be removably couplable with the retractor 1100.

In some embodiments, the retractor connection feature 1230 may comprise a locking feature that may be configured to secure the handle 1200 to the retractor 1100.

In some embodiments, the locking feature may comprise a locking sleeve 1240, a hex socket 1250, and one or more pins or one or more ball detents 1260 that may be configured to lock the handle 1200 to the handle connection feature 1114 of the retractor 1100.

In some embodiments, the locking sleeve 1240 and/or the one or more ball detents 1260 may be spring biased. For example, the locking sleeve 1240 may be spring biased such that the locking sleeve 1240 is pushed distally along the handle shaft 1220. Moreover, the one or more ball detents 1260 may be spring biased such that they are pushed inwardly into the interior space of the hex socket 1250.

In some embodiments, the handle 1200 may be coupled with the retractor 1100 by: (1) translating the locking sleeve 1240 proximally along the handle shaft 1220 to allow the one or more ball detents 1260 to withdraw from the interior space of the hex socket 1250; (2) inserting the hex key 1116 of the handle connection feature 1114 into the hex socket 1250 of the retractor connection feature 1230; and (3) releasing/translating the locking sleeve 1240 distally along the handle shaft 1220 to force the one or more ball detents 1260 to enter into the retention slot 1117 formed in the hex key 1116 to secure the handle 1200 to the retractor 1100.

In some embodiments, the handle 1200 may be decoupled from the retractor 1100 by: (1) translating the locking sleeve 1240 proximally along the handle shaft 1220 to allow the one or more ball detents 1260 to withdraw from the retention slot 1117; and (2) removing the hex key 1116 from the hex socket 1250 to decouple the handle 1200 from the retractor 1100.

Figure 14:
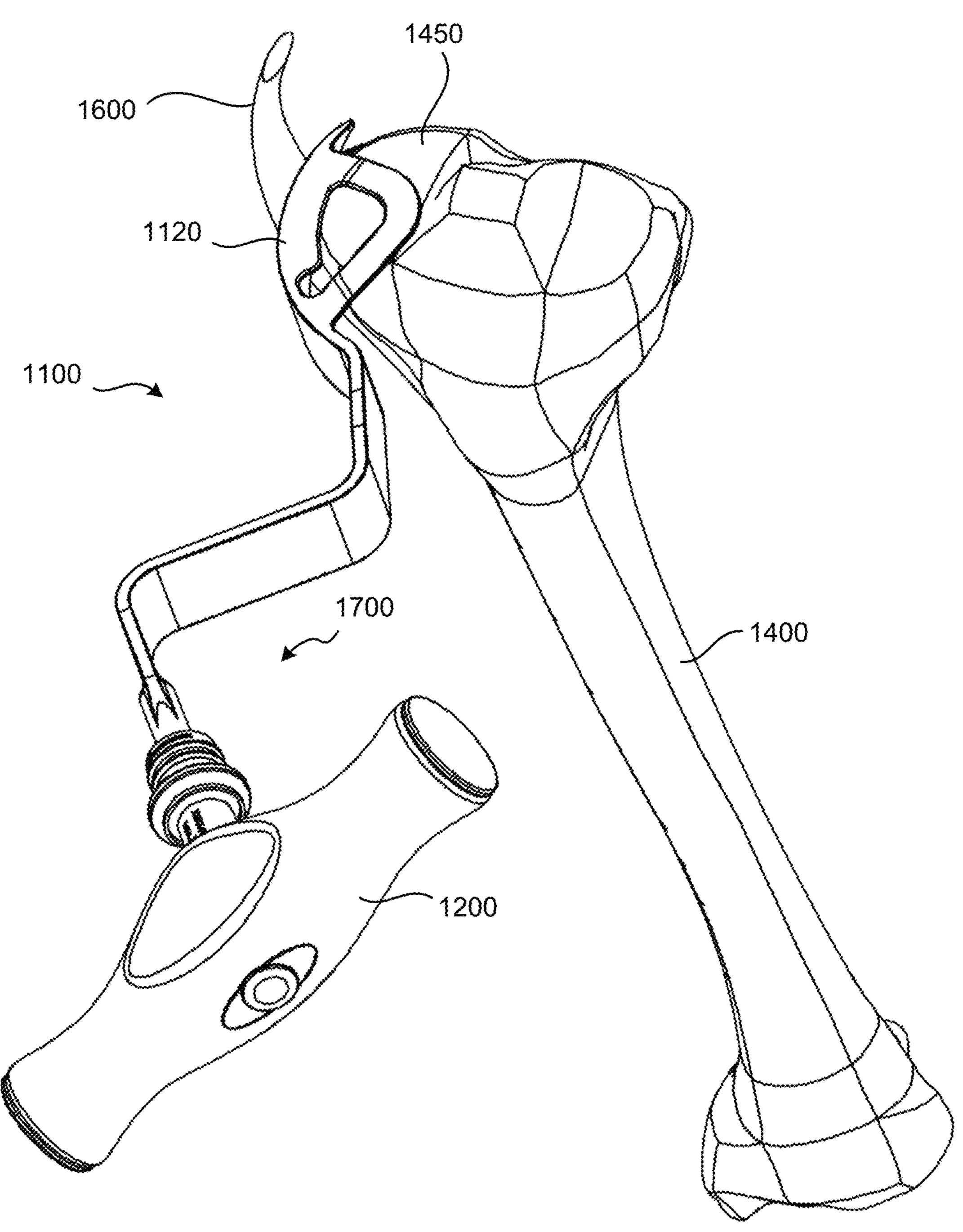
FIG. 14 is another perspective view of FIG. 13 with the femur bone removed.

FIG. 13 is a perspective view of the retractor 1100 coupled to the handle 1200 to form a retractor assembly 1700, with the retractor 1100 inserted into a knee joint 1300 during a surgical procedure. FIG. 14 illustrates another perspective view of FIG. 13 with the femur bone removed to show the retractor member 1120 engaged with the tibial plateau 1450. The knee joint 1300 may include a tibia 1400, a femur 1500, and a medial collateral ligament 1600. As previously described herein, the morphology of the retractor 1100 may help with insertion of the retractor 1100 and/or may help prevent the distal end 1102 of the retractor 1100 from being accidentally placed on the medial side of the medial collateral ligament 1600 during insertion of the retractor 1100 by the surgeon. Rather, the morphology of the retractor 1100 will help ensure that the distal end 1102 of the retractor 1100 will be placed on the lateral side of the medial collateral ligament 1600 by the surgeon during insertion. Once the distal end 1102 of the retractor 1100 has been properly positioned on the lateral side of the medial collateral ligament 1600, the tibial plateau may be resected with a bone saw in a similar manner to that shown and described in FIG. 8. Thus, the retractor 1100 may be utilized by a surgeon to retract a medial collateral ligament of the knee joint away from a tibial plateau during the resection procedure. The cutting shield surface 1136 of the retractor 1100 may also act as a mechanical stop to the blade of a bone saw to further protect the medial collateral ligament from accidental damage or cutting during the tibial plateau resection procedure.

Figure 15:
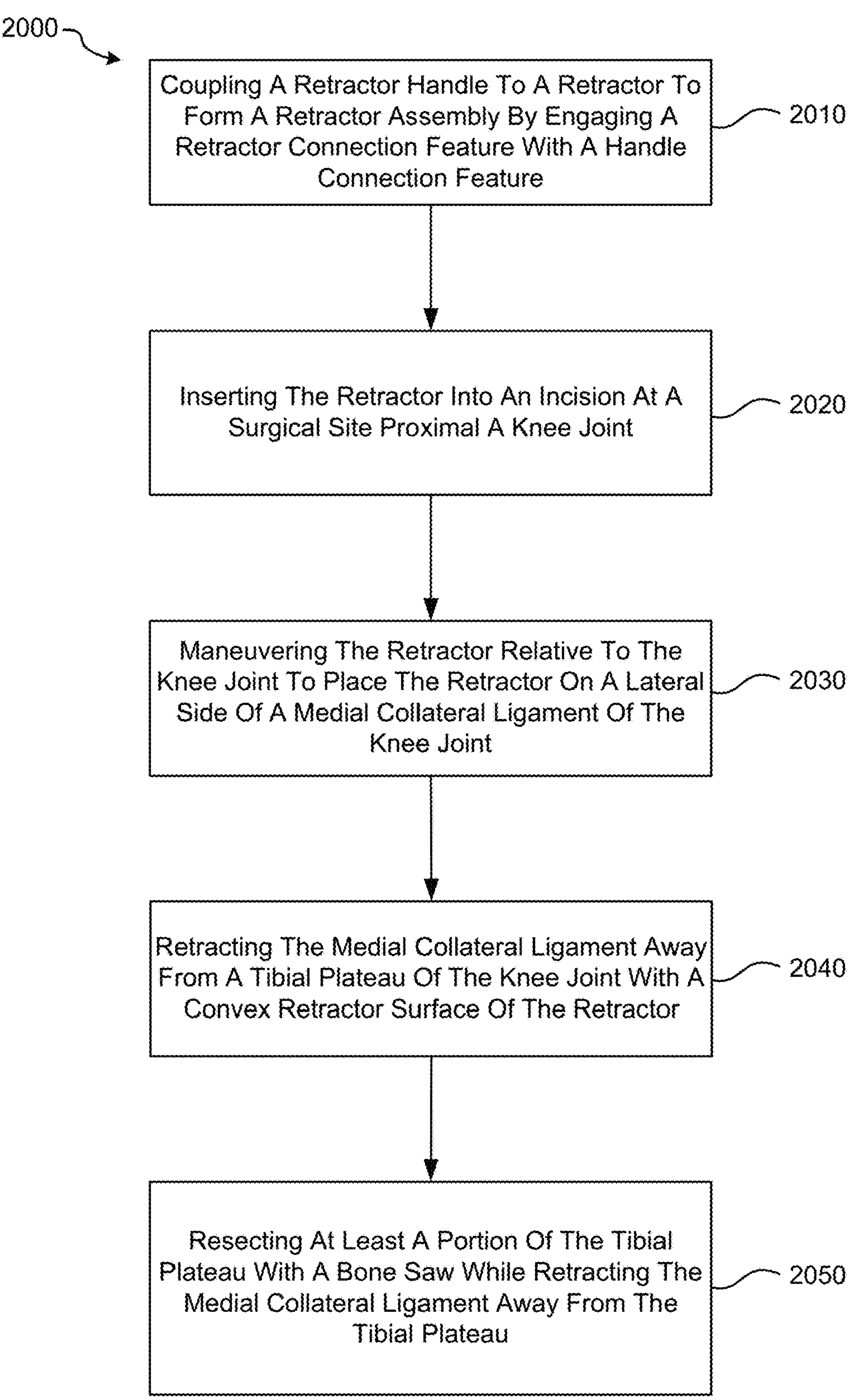
FIG. 15 is a flowchart of a method for retracting a medial collateral ligament with a retractor assembly during a knee joint arthroplasty procedure.

FIG. 15 is a flowchart of a method 2000 for retracting a medial collateral ligament with a retractor assembly 1700 during a knee joint arthroplasty procedure. The retractor assembly 1700 may include a retractor 1100 and a handle 1200. In some embodiments, the retractor 1100 may include a handle connection feature 1114, a guide projection 1150, and an arcuate projection 1130 having a retractor surface 1135 that may be convex and a cutting shield surface 1136 that may be concave. The handle 1200 may include a retractor connection feature 1230 configured to engage the handle connection feature 1114 to removably couple the handle 1200 with the retractor 1100.

The method 2000 may begin with a step 2010 in which a handle 1200 may be coupled to a retractor 1100 to form a retractor assembly 1700 by engaging a retractor connection feature 1230 with a handle connection feature 1114, as previously described herein.

Once the retractor handle 1200 has been coupled to the retractor 1100 to form the retractor assembly 1700, the method 2000 may proceed to a step 2020 in which the retractor 1100 may be inserted into an incision (not shown) at a surgical site proximal the knee joint.

Once the retractor 1100 has been inserted into the incision, the method 2000 may proceed to a step 2030 in which the retractor 1100 may be maneuvered relative to the knee joint in order to place the retractor 1100 on a lateral side of the medical collateral ligament. In some embodiments, the guide projection 1150 and/or the arcuate projection 1130 of the retractor 1100 may traverse inferior to a medial meniscus (not shown) of the knee joint during placement of the of the retractor 1100 with respect to the knee joint. Moreover, in some embodiments positioning the guide projection 1150 of the retractor 1100 over a medial tibial plateau (not shown) of the knee joint may indicate that the arcuate projection 1130 of the retractor 1100 is interposed between the medical collateral ligament and the medial tibial plateau of the knee joint.

Once the retractor 1100 has been placed on the lateral side of the medical collateral ligament, the method 2000 may proceed to a step 2040 in which the surgeon may utilize the retractor surface 1135 of the retractor 1100 to retract the medial collateral ligament away from a tibial plateau of the knee joint.

Alternatively, or in addition thereto, the method 2000 may proceed to a step 2050 in which a portion of the tibial plateau may be resected with a bone saw while the medial collateral ligament is retracted away from the tibia in order to prevent the bone saw from damaging the medial collateral ligament with the cutting shield surface 1136 of the retractor 1100 further preventing the bone saw from damaging the medial collateral ligament, and the method 2000 may end.

In this manner, the medial collateral ligament may be protected from damage by the bone saw during the resection procedure. The retractor 1100 may protect the medial collateral ligament in at least two ways including: (1) via retraction, which increases a separation distance between the bone saw blade and the medial collateral ligament, thus decreasing the likelihood of damaging the medial collateral ligament; and (2) the cutting shield surface 1136 of the retractor 1100 may directly shield the medial collateral ligament from the bone saw blade to prevent the bone saw blade from damaging the medial collateral ligament. Thus, the cutting shield surface 1136 can help in all instances where the separation distance achieved from retraction may or may not be sufficient to keep the medial collateral ligament away from the bone saw blade.

Any methods disclosed herein may comprise one or more steps or actions for performing the described method. One or more of the method steps or actions may be omitted from any of the methods disclosed herein. Moreover, any of the method steps or actions may be interchanged with one another. In other words, unless a specific order of steps or actions is required for proper operation of the embodiment, the order and/or use of specific steps or actions may be modified.

It will also be understood that any of the ligament retractor instruments, components, assemblies, systems, and/or methods that are described herein may be mixed and matched in any number of combinations without departing from the spirit or scope of the present disclosure. For example, the retractor 100 of FIGS. 1A-1I and/or the retractor 1100 of FIGS. 11A-11H may be utilized with the guide rod 200 including any of the hook member 230 embodiments shown in FIGS. 2C-2H, etc. As another non-limiting example, the hook member 230 may be coupled with the guide projection 150 (instead of the guide rod 200) and the attachment aperture 160 may be formed in the guide rod 200 (instead of the guide projection 150), etc. As another non-limiting example, the handle 1200 may be utilized with the retractor 100 and/or the retractor handle 110 may be utilized with the retractor 1100, etc. As another non-limiting example, the guide projections 150 and 1150 may be utilized with any of the retractors 100, 1100 disclosed herein.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles set forth herein.

The phrases "connected to," "coupled to," "engaged with," and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature. The phrase "substantially equal" can mean within about a + or −10% relative variance from one another.

While specific embodiments and applications of the present disclosure have been illustrated and described, it is to be understood that the scope of the appended claims is not limited to the precise configuration and components disclosed herein. Various modifications, changes, and variations which will be apparent to those skilled in the art may be made in the arrangement, operation, and details of the devices, systems, and methods disclosed herein.

What is claimed is:

1. A retractor comprising:

a retractor shaft, the retractor shaft comprising:
  a proximal end; and
  a distal end;
  and
a retractor member disposed at the distal end of the retractor shaft, the retractor member comprising:
  an arcuate projection, the arcuate projection comprising:
    a proximal end coupled to the distal end of the retractor shaft;
    a distal end distal to the proximal end;
    a superior surface;
    an inferior surface;
    a retractor surface extending intermediate the superior surface and the inferior surface, the retractor surface comprising a convex curvature; and
    a cutting shield surface located opposite the retractor surface and extending intermediate the superior surface and the inferior surface; and
a guide projection coupled to the cutting shield surface, the guide projection comprising:
  a superior surface;
  an inferior surface; and
  an aperture formed through the guide projection between the superior surface and the inferior surface;
  wherein the aperture is shaped to receive at least a portion of a femoral condyle therein to position the retractor member relative to a tibial plateau.

2. The retractor of claim 1, wherein the superior surface and the inferior surface of the guide projection are configured to taper toward each other moving from the proximal end of the arcuate projection toward the distal end of the arcuate projection.

3. The retractor of claim 1, wherein the guide projection further comprises an outer edge intermediate the superior surface and the inferior surface.

4. The retractor of claim 3, wherein the outer edge comprises a convex surface.

5. The retractor of claim 1, wherein the distal end of the arcuate projection further comprises:

a first tip;
a second tip; and
a recess intermediate the first tip and the second tip;
wherein at least one of the first tip, the second tip, and the recess is shaped to guide a medial collateral ligament toward the retractor surface as the retractor member is inserted into a knee joint.

6. The retractor of claim 1, further comprising a handle connection feature disposed at the proximal end of the retractor shaft.

7. The retractor of claim 1, wherein the retractor shaft comprises:

a first shaft portion extending along a first longitudinal axis;
a second shaft portion extending along a second longitudinal axis; and
a third shaft portion extending along a third longitudinal axis;
wherein the second shaft portion is intermediate the first shaft portion and the second shaft portion, and the third shaft portion is offset from the first shaft portion.

* * * * *